United States Patent
Basu et al.

(10) Patent No.: US 11,555,010 B2
(45) Date of Patent: *Jan. 17, 2023

(54) DIAMIDE ANTIMICROBIAL AGENTS

(71) Applicants: BROWN UNIVERSITY, Providence, RI (US); BRYANT UNIVERSITY, Smithfield, RI (US)

(72) Inventors: Amit Basu, Barrington, RI (US); Christopher W. Reid, North Kingstown, RI (US); Nola Camille Iwasaki, Southbury, CT (US); Joseph Prete, Pascoag, RI (US)

(73) Assignees: BROWN UNIVERSITY, Providence, RI (US); BRYANT UNIVERSITY, Smithfield, RI (US)

( * ) Notice: Subject to any disclaimer, the term of this patent is extended or adjusted under 35 U.S.C. 154(b) by 125 days.

This patent is subject to a terminal disclaimer.

(21) Appl. No.: 16/937,933

(22) Filed: Jul. 24, 2020

(65) Prior Publication Data
US 2021/0024457 A1   Jan. 28, 2021

Related U.S. Application Data

(60) Provisional application No. 62/878,561, filed on Jul. 25, 2019.

(51) Int. Cl.
| | |
|---|---|
| C07C 233/92 | (2006.01) |
| A61P 31/04 | (2006.01) |
| A61K 31/166 | (2006.01) |
| A61K 45/06 | (2006.01) |
| A61K 31/4465 | (2006.01) |
| C07D 211/34 | (2006.01) |

(52) U.S. Cl.
CPC .......... *C07C 233/92* (2013.01); *A61K 31/166* (2013.01); *A61K 31/4465* (2013.01); *A61K 45/06* (2013.01); *A61P 31/04* (2018.01); *C07D 211/34* (2013.01)

(58) Field of Classification Search
CPC ............................... C07C 233/92; A61P 31/04
See application file for complete search history.

(56) References Cited

U.S. PATENT DOCUMENTS

| | | | |
|---|---|---|---|
| 4,610,983 A | 9/1986 | Takagawa et al. | |
| 5,007,790 A | 4/1991 | Shell | |
| 5,169,645 A | 12/1992 | Shukla et al. | |
| 5,322,858 A | 6/1994 | Canfield et al. | |
| 5,582,837 A | 12/1996 | Shell | |
| 5,780,498 A | 7/1998 | Saika et al. | |
| 5,972,389 A | 10/1999 | Shell | |
| 6,323,219 B1 | 11/2001 | Costanzo | |
| 6,340,475 B2 | 1/2002 | Shell et al. | |
| 6,441,042 B1 | 8/2002 | Hunter et al. | |
| 6,451,808 B1 | 9/2002 | Cowles | |
| 6,488,962 B1 | 12/2002 | Berner et al. | |
| 6,716,878 B1 | 4/2004 | Todd et al. | |
| 10,829,440 B2* | 11/2020 | Basu | A61K 31/165 |
| 2002/0051820 A1 | 5/2002 | Shell et al. | |
| 2003/0039688 A1 | 2/2003 | Shell et al. | |
| 2003/0044466 A1 | 3/2003 | Markey et al. | |
| 2003/0104053 A1 | 6/2003 | Gusler et al. | |
| 2003/0104062 A1 | 6/2003 | Berner et al. | |
| 2003/0147952 A1 | 8/2003 | Lim et al. | |
| 2006/0040871 A1 | 2/2006 | Levey et al. | |
| 2009/0163545 A1 | 6/2009 | Goldfarb | |
| 2013/0331456 A1 | 12/2013 | Basu et al. | |

FOREIGN PATENT DOCUMENTS

| | | |
|---|---|---|
| CN | 101250167 A | 8/2008 |
| CN | 101875645 A | 11/2010 |
| WO | 90/11757 A1 | 10/1990 |
| WO | 93/18755 A1 | 9/1993 |
| WO | 97/47285 A1 | 12/1997 |
| WO | 98/11879 A1 | 3/1998 |
| WO | 98/55107 A1 | 12/1998 |
| WO | 01/32217 A2 | 5/2001 |
| WO | 01/56544 A2 | 8/2001 |
| WO | 01/97783 A1 | 12/2001 |
| WO | 02/32416 A2 | 4/2002 |
| WO | 02/096404 A1 | 12/2002 |
| WO | 03/035029 A1 | 5/2003 |
| WO | 03/035039 A1 | 5/2003 |

(Continued)

OTHER PUBLICATIONS

International Search Report and Written Opinion for Application No. PCT/US2016/036972 dated Sep. 2, 2016.

Kuhn et al., "Anti-Bacterial Glycosyl Triazoles-ldentification of an N-acetylglucosamine derivative with Bacteriostatic Activity Agains Bacillus", DOI: 10.1039/c4md00127c, In MedChem Communication, vol. 5, 2014, pp. 1213-1217.

Santos et al., "Palladium-Catalyzed Ring Opening of Aminocyclopropyl Ugi Adducts", DOI: 10.1055/s-0031-1290312. Art ID: D66411ST, vol. 23, No. 3, Jan. 19, 2012, pp. 438-442.

(Continued)

*Primary Examiner* — Golam M Shameem
(74) *Attorney, Agent, or Firm* — Adler Pollock & Sheehan P.C.; Vinit Kathardekar

(57) ABSTRACT

This invention is directed to compounds of Formula (I)

Formula I

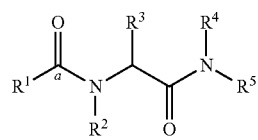

pharmaceutically acceptable salts, esters, and prodrugs thereof, to their preparation, to pharmaceutical compositions comprising compounds of Formula I, and to their uses as antimicrobial agents.

19 Claims, 4 Drawing Sheets

(56) References Cited

FOREIGN PATENT DOCUMENTS

| WO | 03/035040 A1 | 5/2003 | | |
|---|---|---|---|---|
| WO | 03/035041 A1 | 5/2003 | | |
| WO | 03/035177 A2 | 5/2003 | | |
| WO | 2012/004554 A1 | 1/2012 | | |
| WO | 2016/201288 A1 | 12/2016 | | |
| WO | WO-2016201288 A1 * | 12/2016 | ........... | A61K 31/165 |
| WO | 2017/223349 A1 | 12/2017 | | |
| WO | 2018/237268 A1 | 12/2018 | | |

OTHER PUBLICATIONS

STN Registry database entry for CAS RN 1033547-46-4, entry date Jul. 11, 2008, Accessed Aug. 9, 2019, 1 page.

Ito et al., "A Medium-Term Rat Liver Bioassay for Rapid in Vivo Detection of Carcinogenic Potential of Chemicals", vol. 94, No. 1, Jan. 2003, pp. 3-8.

Chou et al., "Quantitative Analysis of Dose-Effect Relationships: The Combined Effects of Multiple Drugs or Enzyme Inhibitors", Advances in Enzyme Regulation, vol. 22, 1984, pp. 27-55.

Hacker et al., "Pharmacology: Principles and Practice", Academic Press, Chapter 10, Jun. 19, 2009, pp. 216-217.

Holford et al., "Understanding the Dose-Effect Relationship: Clinical Application of Pharmacokinetic-Pharmacodynamic Models", Clin Pharmacokinet, vol. 6, No. 6, 1981, pp. 429-453.

Hong et al., "Atomic-Scale Detection of Organic Molecules Coupled to Single-Walled Carbon Nanotubes", J_Am. Chem. Soc., vol. 129, Aug. 16, 2007, pp. 10966-10967.

Horsburgh et al., "LytG of Bacillus Subtilis Is a Novel Peptidoglycan Hydrolase: The Major Active Gucosaminidase", Biochemistry, vol. 42, No. 2, Dec. 19, 2002, pp. 257-264.

Loewe et al., "Effect of Combinations: Mathematical Basis of Problem", Arch. Exp. Pathol. Pharmacol, vol. 114, 1926, pp. 313-326.

Palomino et al., "Resazurin Microtiter Assay Plate: Simple and Inexpensive Method for Detection of Drug Resistance in Mycobacterium Tuberculosis", Antimicrobial Agents and Chemotherapy, vol. 46, No. 8, Aug. 2002, pp. 2720-2722.

Nayyab et al., "Diamide inhibitors of the Bacillus subtilis N-acetylglucosaminidase LytG that exhibit anti-bacterial activity", ACS infectious diseases, vol. 3, No. 6, Jun. 9, 2017, pp. 421-427.

Chandio et al., "Synthesis and Antimicrobial Assessment of $Fe^{3+}$ Inclusion Complex of p-tert-Butylcalix[4]arene Diamide Derivative", https//doi.org/10.1155/2019/2S34072, Journal of Chemistry, Mar. 28, 2019, pp. 1-9.

International Search Report and Written Opinion for Application No. PCT/US2018/039001 dated Sep. 14, 2018.

Carey et al., "Advanced Organic Chemistry", Part A: Structure and Mechanisms, Fifth Edition, 2007, 1212 pages.

"Fieserand Fieser's Reagents for Organic Synthesis", John Wiley and Sons, vols. 1-17, 1991.

"Organic Reactions", John Wiley and Sons, vols. 1-40, 1991.

"Rodd's Chemistry of Carbon Compounds", Elsevier Science Publishers, vol. 1-5, 1989.

Greene et al., "Protective Groups in Organic Synthesis", Third Edition, John Wiley & Sons, INC., 1999, 52 pages.

Yuan et al., "Tetrahedron", vol. 72, 2016, pp. 338-336.

* cited by examiner

DIAMIDE ANTIMICROBIAL AGENTS

CROSS-REFERENCE TO RELATED APPLICATIONS

This application claims benefit from U.S. Provisional Patent Application No. 62/878,561 filed Jul. 25, 2019, which is incorporated herein by reference in its entirety.

STATEMENT REGARDING FEDERALLY SPONSORED RESEARCH

This invention was made with government support under grant number P20GM103430 awarded by an Institutional Development Award (IDeA) from the NIGMS of the NIH. The government has certain rights in the invention

BACKGROUND OF THE INVENTION

Methods for the growth-inhibition and destruction of bacteria have long been a key area of study towards the improvement of human health. Numerous antibacterial agents have been designed and manufactured, but many are now exhibiting decreased efficacy due to microbial resistance. The Centers for Disease Control estimates that at least a quarter of a million illnesses and 23,000 deaths over the past year in the U.S. were due to antibiotic resistance. A report published in 2009 by the Alliance for the Prudent Use of Antibiotics (APUA) estimated that over $20 billion dollars per year is consumed by healthcare costs to treat antibiotic-resistant infections. Although these figures could be improved by addressing the misuse and overuse of antibiotics in the clinic, an understanding of the mechanisms by which bacteria develop resistance and designing drugs to circumvent these is essential for the treatment of millions of infections.

There are three general molecular mechanisms that confer antibiotic resistance. The first is the inclusion of efflux pumps into the membrane of the bacteria. These pumps prevent the accumulation of intracellular-acting antibiotics such as protein synthesis inhibitors by actively pumping them out of the cytoplasm. Efflux pumps are generally adapted from existing membrane pumps used either to move lipophilic molecules in and out of the bacteria or rapidly expel naturally produced antibiotics meant to destroy neighboring bacteria. Drugs such as tetracyclines and erythromycins frequently fail to reach therapeutic concentrations due to expulsion through efflux pumps. A second method used by bacteria is to either destroy or modify the chemically relevant features of the antibiotic. This can include the cleavage of bonds within the antibiotic or chemical modification of groups on the antibiotic.

The third most method of resistance does not act on the inhibitor at all, but instead modifies the target of inhibition. By reprogramming the target structure, bacteria can reduce the efficacy of the antibiotic while retaining the inherent function of the target. Further, bacteria develop into colonies that adhere to a surface within a dense extracellular matrix consisting of DNA, proteins, and polysaccharides, known as a biofilm. Biofilms are pervasive in implanted medical devices and damaged tissue, leading to unresolved infections.

Though plagued by numerous resistance issues, cell wall-acting antibiotics are the most prevalent inhibitors of bacterial growth, such as penicillin. In particular, potent antibiotics target the synthesis of peptidoglycan, a key component of the bacterial cell wall. Peptidoglycan resists internal turgor, mediates cell growth and division, defines the shape of the cell, and helps to anchor proteins and glycoproteins to the cell wall.

Peptidoglycan consists of the aminoglycosides N-acetylglucosamine (GlcNAc) and N-acetylmuramic acid (MurNAc) linked in alternating chains through $\beta$-(1-4) bonds. In *Bacillus subtilis*, each individual chain is between 50 and 250 disaccharide units. These linear glycan chains are cross-linked by short and variable peptide strands. The D-lactoyl group of MurNAc is amidated by a tetrapeptide in the mature macromolecule. Cross-linking of these peptides allows for the formation of a mesh-like matrix that surrounds the cell.

The cell wall has been a prominent target largely due to its absence in mammalian cells. Inhibitors designed for cell wall synthesis ideally only affect bacterial infections and do not damage host cells. Of the large number of cell wall synthesis inhibitors currently being developed and marketed, almost all fall into two major classes: $\beta$-lactams and macrocyclic polypeptides.

$\beta$-Lactams comprise penicillins and cephalosporins use a reactive warhead (a four-membered lactam ring) to bind irreversibly to bacterial transpeptidases involved in assembly of the cross-bridge peptide chains within the peptidoglycan. Bacteria employ enzymes called $\beta$-lactamases to destroy the warhead, opening the lactam ring and rendering the antibiotic ineffective.

Macrocyclic polypeptides include compounds like vancomycin. Vancomycin acts by tying up the peptide substrates used by transpeptidases and prevents their use as building blocks. Vancomycin's target, though, is the highly variable peptide cross-bridge that is readily modified by bacteria, thus preventing binding of vancomycin and eliminating its potential activity.

Additionally, macrocyclic polypeptide drugs pose a serious problem to synthetic chemists, due to their complexity. Presently, there are no successful antibiotics that target the natural recycling of the peptidoglycan. This hydrolytic breakdown and remodeling of the cell wall is carried out by a set of bacterial enzymes termed "autolysins" that are heavily implicated in peptidoglycan maturation, cell separation and expansion, motility, cell-wall turnover, and protein secretion. Within a single generation of bacterial growth, 50% of the peptidoglycan layer is removed and recycled by the activity of autolysins.

During vegetative growth of *Bacillus subtilis*, for example, two major enzymes present in the cell wall are involved with the autolytic activity occurring within the peptidoglycan: N-acetylmuramoyl-L-alanine amidase (amidase) and endo-$\beta$-N-acetylglucosaminidase (GlcNAcase). These enzymes are encoded by the LytC and LytD genes respectively and are regulated by the σD transcription factor. Despite their substantial expression and cell-wall localization during exponential growth, neither of these enzymes is individually crucial to the survival or even proper cell-wall turnover of the cell. Furthermore, the double-knockout mutant of LytC/LytD had no reduction in cell separation and incomplete reduction in cell-wall turnover. The mutual compensatory nature of autolytic enzymes complicates any attempts to develop autolysin inhibitors as antibiotics.

Several compounds have some inhibitory activity against purified autolysins but all have failed to exhibit any bacteriostatic or bactericidal effect. The $\beta$-hexosaminidase inhibitor, NAG-thiazoline, was only a weak binder of LT and had no effect on the viability of *E. coli*. Analogues of 2-acetamido-2-deoxynojirimycin were not active in vivo even at 1 mM. Targeting autolysin enzymes that which act on the invariant glycan chain may drastically reduce the potential for development of resistance.

There is a need in the art to identify novel compounds that can be used to treat or prevent bacterial infections in a subject. Treatment with such compounds should be efficacious and prone to minimal resistance build-up, or no resistance at all. The present invention addresses and meets this need.

SUMMARY OF THE INVENTION

This invention is directed to compounds of Formula (I), to the pharmaceutically acceptable salts, esters, and prodrugs thereof, to their preparation, to pharmaceutical compositions comprising compounds of Formula I, and to their uses as antimicrobial agents. In one aspect, the instant invention is directed to a compound of Formula I:

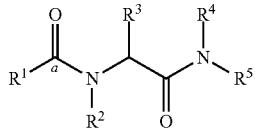

Formula I wherein:

$R^1$ represents a substituent selected from a group selected from polyethyleneglycol, hydrogen, $C_1$-$C_6$ alkyl, and aryl, wherein said $R^1$ substituents, except when $R^1$ represents hydrogen, are independently substituted with 1 to 3 substituents selected from a group consisting of H, X, $S(C_{1-6}$ alkyl), $O(C_{1-6}$ alkyl), and $CX_3$;

$R^2$ represents a substituent selected from a group consisting of $C_1$-$C_8$ alkyl, hydrogen, $C_3$-$C_8$ cycloalkyl, allyl, $C_3$-$C_8$ hetero cycloalkyl, polyethyleneglycol, propargyl, homopropargyl, aryl, heteroaryl, arylalkyl, and heteroarylalkyl, wherein each of said $R^2$ substituents, except when $R^2$ represents hydrogen, are independently substituted with 1-3 substituents selected from a group consisting of $C_1$-$C_6$ alkyl, H, $(CH_2$—O—$(CH_2)_{1-4})_6$—OH, $C_1$-$C_6$ alkenyl, $C_1$-$C_6$ alkynyl, OH, $O(C_1$-$C_6$ alkyl), F, Cl, Br, I, $NO_2$, —C(=O)H, —C(=O)OH, —C(=O)O($C_1$-$C_6$ alkyl), —C(=O)$NH_2$, —C(=O)NH($C_1$-$C_6$ alkyl), and —C(=O)N($C_1$-$C_6$ alkyl)($C_1$-$C_6$ alkyl);

$R^3$ represents a substituent selected from a group consisting of $C_{1-6}$ alkyl-$NH_2$, hydrogen, $CH(CH_3)$—$NH_2$, $CH(CH_2CH_3)$—$NH_2$, $CH(CH_2CH_2CH_3)$—$NH_2$, $CH(CH_2CH_2CH_2CH_3)$—$NH_2$, $(CH_2)_{0-3}$— $C_3$-$C_8$ hetero cycloalkyl, $C_3$-$C_8$ cycloalkyl, propargyl, homopropargyl, polyethylene glycol, aryl, and heteroaryl, wherein each $R^3$ substituent, except when $R^3$ represents hydrogen, is independently substituted with 1-3 substituents independently selected from a group consisting of H, $C_1$-$C_6$ alkyl, OH, $O(C_1$-$C_6$ alkyl), F, Cl, Br, I, $NO_2$, —C(=O)H, —C(=O) OH, —C(=O)O($C_1$-$C_6$ alkyl), —C(=O)$NH_2$, —C(=O)NH($C_1$-$C_6$ alkyl), and —C(=O)N($C_1$-$C_6$ alkyl)($C_1$-$C_6$ alkyl);

$R^4$ represents a substituent selected from the group consisting of $C_1$-$C_6$ alkyl, hydrogen, alkyl-aryl, $C_3$-$C_8$ cycloalkyl, arylalkyl, and heteroaryl-alkyl, wherein each of the $R^4$ substituents, except when $R^4$ represents hydrogen, is independently substituted with 1-3 substituents independently selected from the group consisting of $C_1$-$C_6$ alkyl, H, OH, $O(C_1$-$C_6$ alkyl), F, Cl, Br, I, $NO_2$, —C(=O)H, —C(=O) OH, —C(=O)O($C_1$-$C_6$ alkyl), —C(=O)$NH_2$, —C(=O) NH($C_1$-$C_6$ alkyl), and —C(=O)N($C_1$-$C_6$ alkyl)($C_1$-$C_6$ alkyl);

$R^5$ is H or methyl; and

X is selected from Cl, I, Br, and F.

A preferred embodiment provides a compound of Formula I wherein, $R^1$ has at least one substituent ortho to the carbonyl group, wherein the at least one substituent is selected from the group consisting of X, $S(C_1$-$C_6$ alkyl), $O(C_{1-6}$ alkyl), and $CX_3$. Another preferred embodiment provides a compound of Formula I wherein the at least one substituent ortho to the carbonyl group is selected from the group consisting of X, $O(C_{1-64}$ alkyl), and $CF_3$.

In yet another embodiment is provided a compound of Formula I wherein $R^2$ is selected from the group consisting of $C_1$-$C_6$ alkyl, $C_5$-$C_6$ cycloalkyl, polyethyleneglycol, propargyl, homopropargyl, phenyl, heteroaryl, aryl-$(CH_2)_{1-2}$—, and heteroaryl-$(CH_2)_{1-2}$—, wherein each of the said $R^2$ groups are independently substituted with 1-3 substituents independently selected from the group consisting of $C_1$-$C_6$ alkyl, $(CH_2$—O—$(CH_2)_2)_6$—OH, H, OH, $O(C_1$-$C_6$ alkyl), F, Cl, Br, I, and $NO_2$, and a further preferred embodiment provides a compound of Formula I wherein $R^2$ is selected from the group consisting of $C_1$-$C_4$ alkyl, cyclo-hexyl, phenyl, o-iodophenyl, o-bromophenyl, o-chlorophenyl, o-fluorophenyl, o-methoxyphenyl, p-iodophenyl, p-bromophenyl, p-chlorophenyl, p-fluorophenyl, p-methoxyphenyl, benzyl, $Ph(CH_2)_2$—, $Ph_2CHCH_2$—, and —$CH(CH_3)Ph$.

Another preferred embodiment provides a compound of Formula I wherein $R^3$ is selected from the group consisting of $C_{1-4}$ alkyl-$NH_2$, $CH(CH_3)$—$NH_2$, $CH(CH_2CH_3)$—$NH_2$, $CH(CH_2CH_2CH_3)$—$NH_2$, $CH(CH_2CH_2CH_2CH_3)$—$NH_2$, $(CH_2)_{0-1}$—$C_4$-$C_6$-heterocycloalkyl, $C_4$-$C_6$ cycloalkyl, aryl, and heteroaryl, wherein each $R^3$ group is independently substituted with 1-2 substituents selected from the group consisting of $C_1$-$C_6$ alkyl, OH, $O(C_1$-$C_6$ alkyl), F, Cl, Br, I, H, $NO_2$, —C(=O)H, —C(=O)OH, —C(=O)O($C_1$-$C_6$ alkyl), —C(=O)$NH_2$, —C(=O)NH($C_1$-$C_6$ alkyl), and —C(=O)N($C_1$-$C_6$ alkyl)($C_1$-$C_6$ alkyl).

Yet another preferred embodiment provides a compound of Formula I wherein $R^4$ is selected from the group consisting of $C_1$-$C_6$ alkyl, cyclo-hexyl, benzyl, wherein each of the alkyl, cyclo-hexyl, and benzyl group is substituted with 1-2 substituents independently selected from the group consisting of $C_1$-$C_3$ alkyl, H, OH, $O(C_1$-$C_3$ alkyl), F, Cl, Br, and I.

A further preferred embodiment provides a compound of Formula I wherein, $R^1$ represents an aryl group, said aryl group substituted with X; $R^2$ is selected from $CH_2$—$(CH_2$—O—$(CH_2)_2)_6$—OH, $C_3$-$C_8$ cycloalkyl, and polyethyleneglycol; $R^3$ is selected from a group consisting of $C_{1-6}$ alkyl-$NH_2$, $CH(CH_3)$—$NH_2$, $CH(CH_2CH_3)$—$NH_2$, $CH(CH_2CH_2CH_3)$—$NH_2$, $CH(CH_2CH_2CH_2CH_3)$—$NH_2$, and $(CH_2)_{0-1}$-heterocyclyl; $R^4$ represents cyclo-hexyl; $R^5$ represents H; and X represents I, Cl, or Br.

A particularly preferred aspect of the present invention provides a compound of Formula I wherein, $R^1$ represents an aryl group, said aryl group substituted with X;

$R^2$ represents $C_4$-$C_8$ cycloalkyl;

$R^3$ is selected from a group consisting of $C_{1-6}$ alkyl-$NH_2$, $CH(CH_3)$—$NH_2$, $CH(CH_2CH_3)$—$NH_2$, $CH(CH_2CH_2CH_3)$—$NH_2$, $CH(CH_2CH_2CH_2CH_3)$—$NH_2$, and $(CH_2)_{0-1}$-heterocyclyl;

$R^4$ represents cyclo-hexyl;

$R^5$ represents H; and

X represents I, Cl, or Br.

Preferred compound of Formula I is selected from:
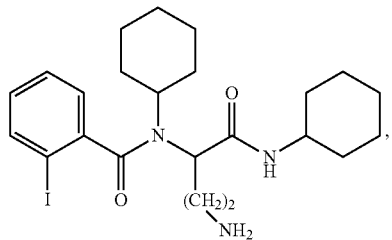,
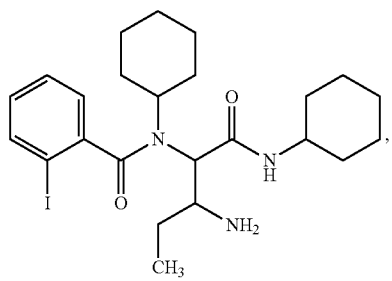,
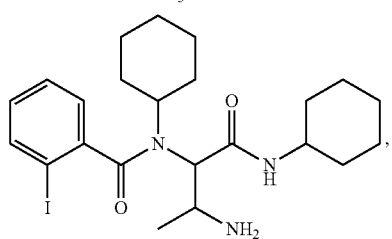,
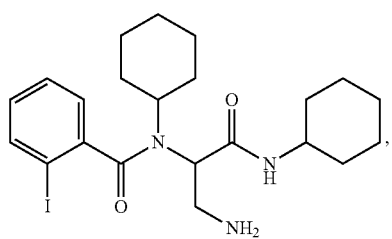,
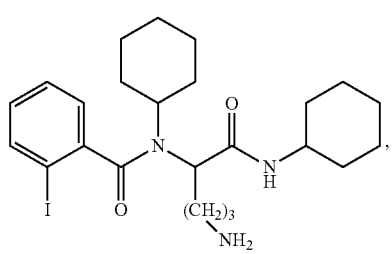,
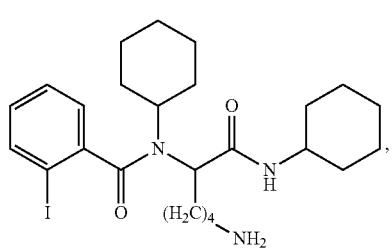,
-continued
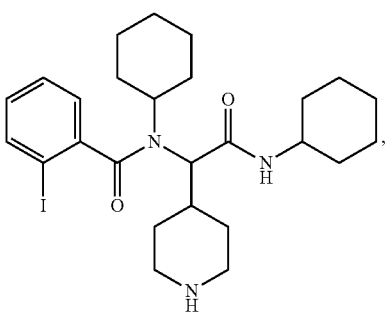,
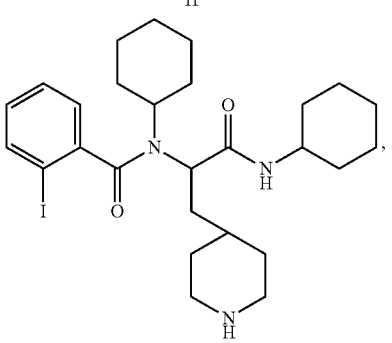,
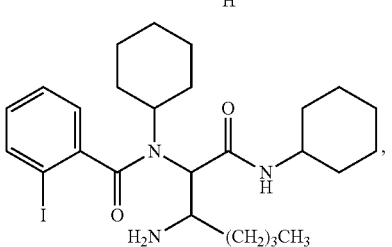,
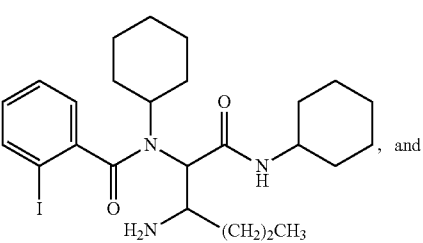, and
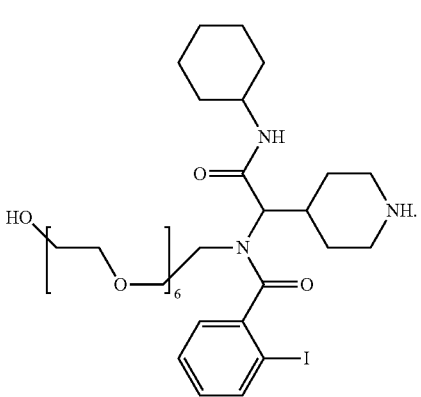.

Particularly preferred is a compound of Formula I selected from,

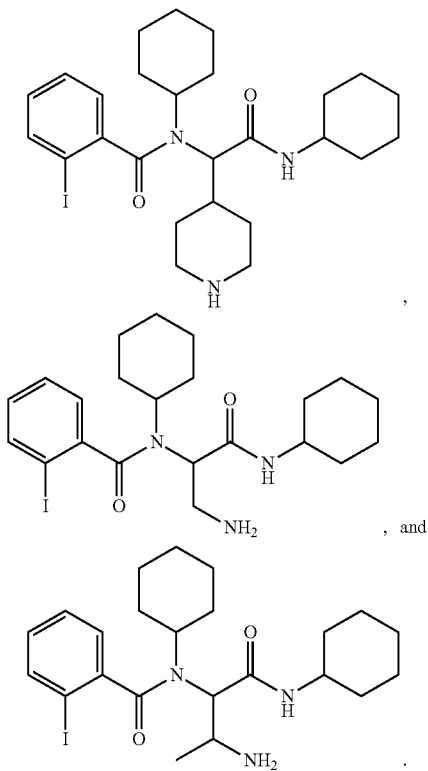

, and

Another aspect of the present invention provides a salt of a compound of Formula I, wherein the salt is an acid addition salt and is selected from the group consisting of sulfate, hydrogen sulfate, hydrochloric, hydrobromic, hydriodic, nitric, carbonic, sulfuric, phosphoric, formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, p-hydroxybutyric, salicylic, galactaric and galacturonic acid, and any combinations thereof.

Yet another aspect of the present invention provides a salt of a compound of Formula I wherein the salt is a base addition salt and is selected from the group consisting of calcium, magnesium, potassium, sodium, ammonium, zinc, a basic amine salt, and any combinations thereof, wherein the basic amine is selected from the group consisting of triethylamine, diisopropylethylamine, trimethylamine, N,N'-dibenzylethylene-diamine, chloroprocaine, choline, diethanolamine, ethylenediamine, meglumine, procaine and any combinations thereof.

Provided in yet another aspect of the present invention is a method of inhibiting N-acetylglucosaminidase in a cell, the method comprising contacting the cell with a compound of Formula I. Provided in a preferred aspect is a method of inhibiting a N-acetylglucosaminidase in the cytosol of a cell, the method comprising contacting the N-acetylglucosaminidase with any of the compounds of Formula I, wherein further preferred is a method wherein the N-acetylglucosaminidase is derived from a bacterium, or a fungus, and an even further preferred method is wherein the N-acetylglucosaminidase comprises an autolysin.

A further preferred aspect of the present invention provides a method of inhibiting N-acetylglucosaminidase by contacting the cell with a compound of Formula I wherein the bacterium is Gram-positive, and even further preferred is a method wherein the Gram-positive bacterium is selected from the group consisting of *Streptococcus* sp., *Staphylococcus* sp., *Enterococcus* sp., *Corynebacterium* sp., *Listeria* sp., *Clostridium* sp., *Bacillus* sp, *Clostridium difficile, Streptococcus pneumoniae, Staphylococcus aureus*, vancomycin intermediate resistance *S. aureus* (VISA), *Enterococcus faecalis*, vancomycin resistant enterococci (VRE), *Streptococcus pyogenes, Bacillus anthracis, Corynebacterium diphtheria* and *Bacillus cereus*.

Another preferred embodiment provides a method of inhibiting N-acetylglucosaminidase by contacting the cell with a compound of Formula I wherein the bacterium is Gram-negative and is selected from a group consisting of *Salmonella* sp., *Escherichia* sp., *Klebsiella* sp., *Acinetobacter* sp., *Pseudomonas* sp., *Vibrio* sp. *Enterobacter* sp, *Salmonella enterica, Salmonella typhii, Escherichia coli, Klebsiella pneumoniae, Acinetobacter baumannii* and *Pseudomonas aeruginosa*.

Another aspect of the present invention provides a method of treating or preventing a bacterial infection in a subject comprising administering to a subject in need thereof a therapeutically effective amount of a compound of Formula I thereby treating or preventing a bacterial infection in a subject.

Another aspect of the present invention provides a method of treating or preventing a bacterial infection in a subject comprising administering to a subject in need thereof a therapeutically effective amount of a compound of Formula I along with at least one additional antibacterial agent.

Yet another aspect of the present invention provides a method of treating or preventing a bacterial infection in a subject comprising administering to a subject in need thereof a therapeutically effective amount of a compound of Formula I, wherein the subject is a mammal, and in particular wherein the mammal is a human.

Another aspect of the present invention provides a prepackaged pharmaceutical composition comprising a compound of Formula I, including a compound of Formula I in one of the preferred embodiments, a salt or solvate thereof and an instructional material for use thereof. A further preferred aspect provides a prepackaged pharmaceutical composition wherein the instructional material comprises instructions for preventing or treating a bacterial infection in a subject, and yet further preferred is a prepackaged pharmaceutical composition comprising an applicator.

In certain embodiments, the salt of any compound disclosed herein is an acid addition salt and is selected from the group consisting of sulfate, hydrogen sulfate, hydrochloric, hydrobromic, hydriodic, nitric, carbonic, sulfuric, phosphoric, formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, p-hydroxybutyric, salicylic, galactaric and galacturonic acid, and any combinations thereof.

The invention further provides a method of inhibiting a N-acetylglucosaminidase in a cell comprising contacting the cell with a compound of the invention. In certain embodiments, the cell is a bacterium, a fungus or a cancer cell. In yet other embodiments, the N-acetylglucosaminidase comprises an autolysin.

The invention also provides a method of inhibiting a N-acetylglucosaminidase in the cytosol of a cell. In certain embodiments, the method comprises contacting the N-acetylglucosaminidase with at least one compound of the invention. In other embodiments, the N-acetylglucosaminidase is derived from a bacterium, a fungus or a cancer cell. In yet other embodiments, the N-acetylglucosaminidase comprises an autolysin.

The invention further provides a method of treating or preventing a bacterial infection in a subject comprising administering to a subject in need thereof a therapeutically effective amount of at least one compound of the invention, thereby treating or preventing a bacterial infection in the subject.

DETAILED DESCRIPTION OF THE INVENTION

Figure 1:
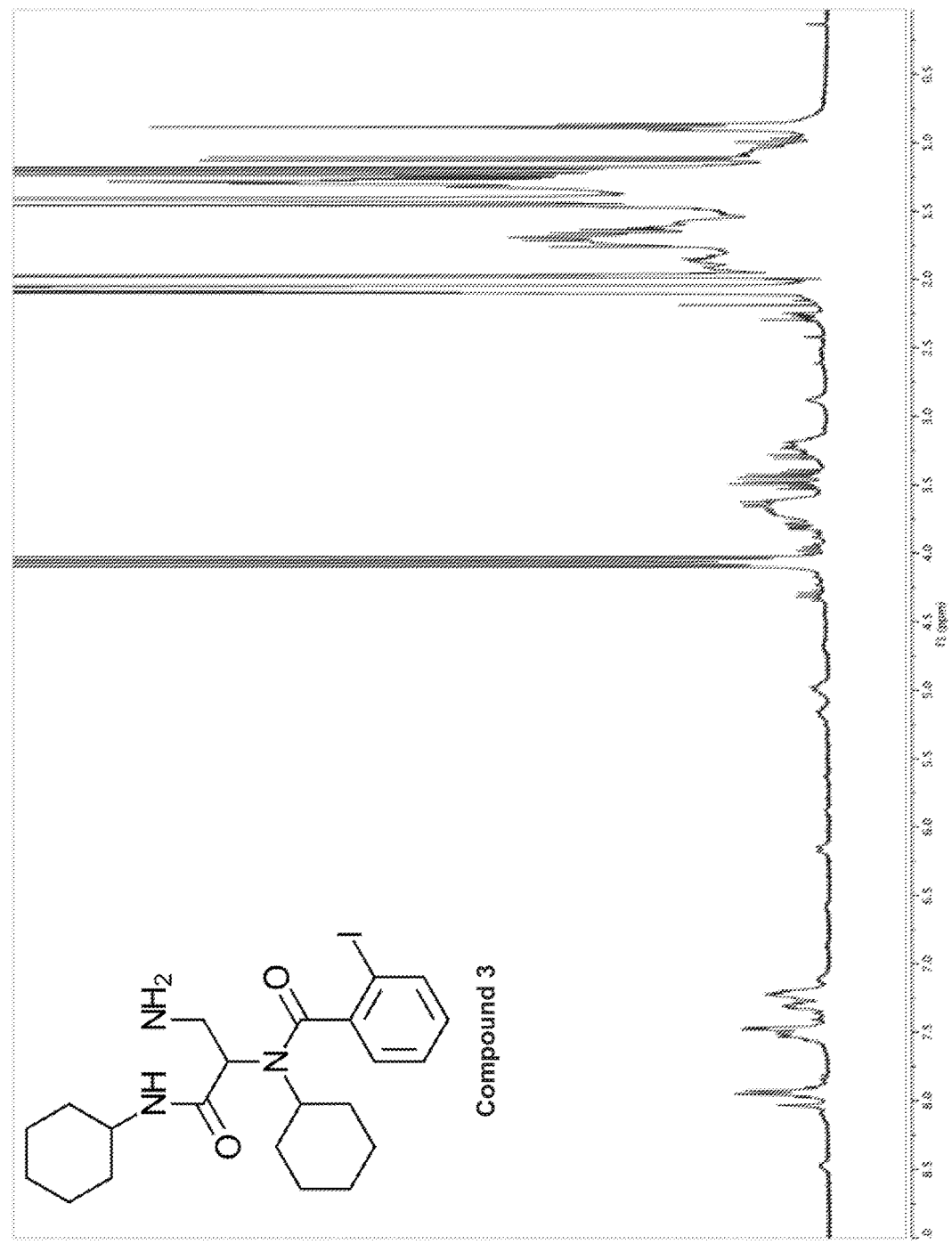
FIG. 1 is a proton NMR of compound 3.
Figure 2:
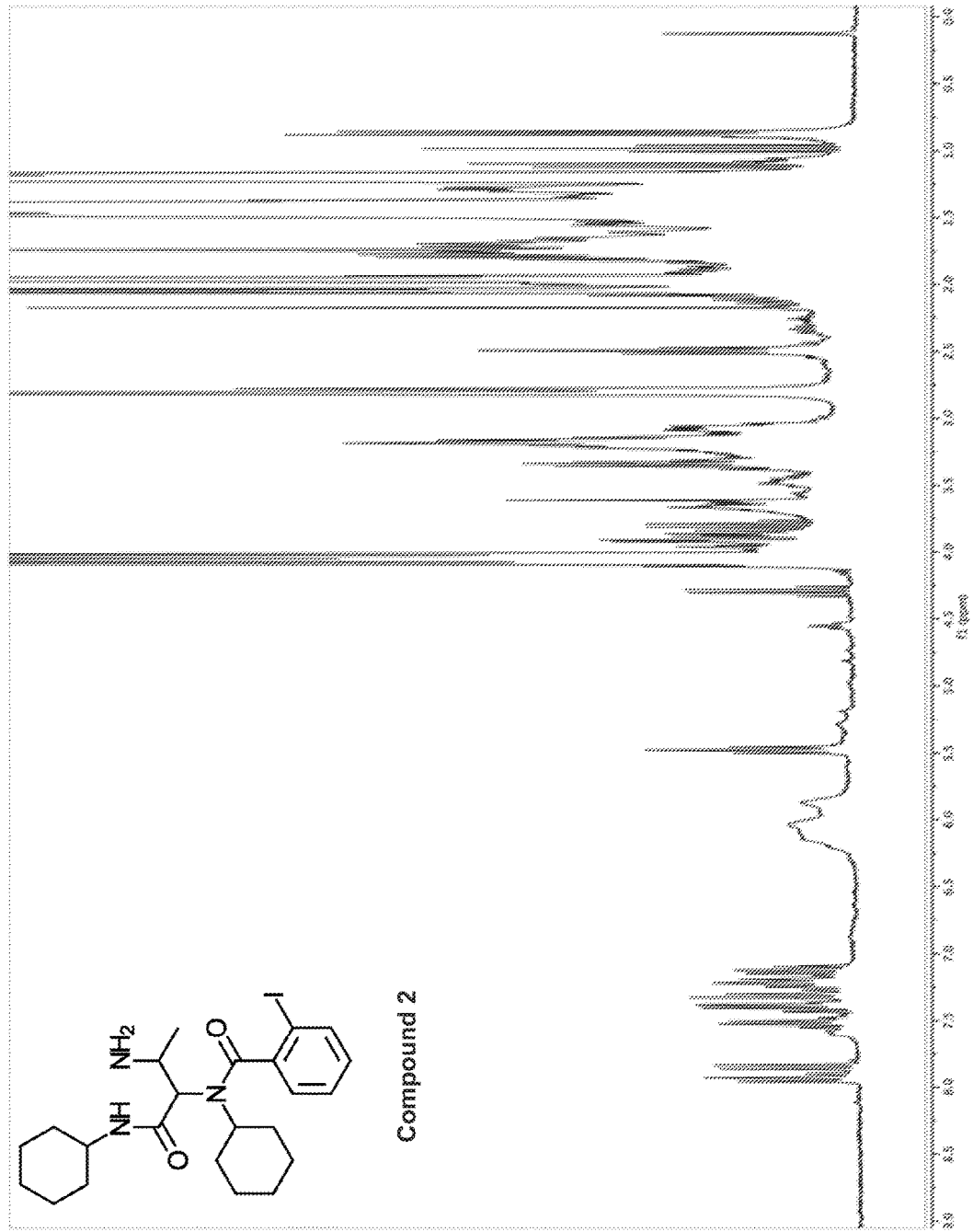
FIG. 2 represents the proton NMR of compound 2.
Figure 3:
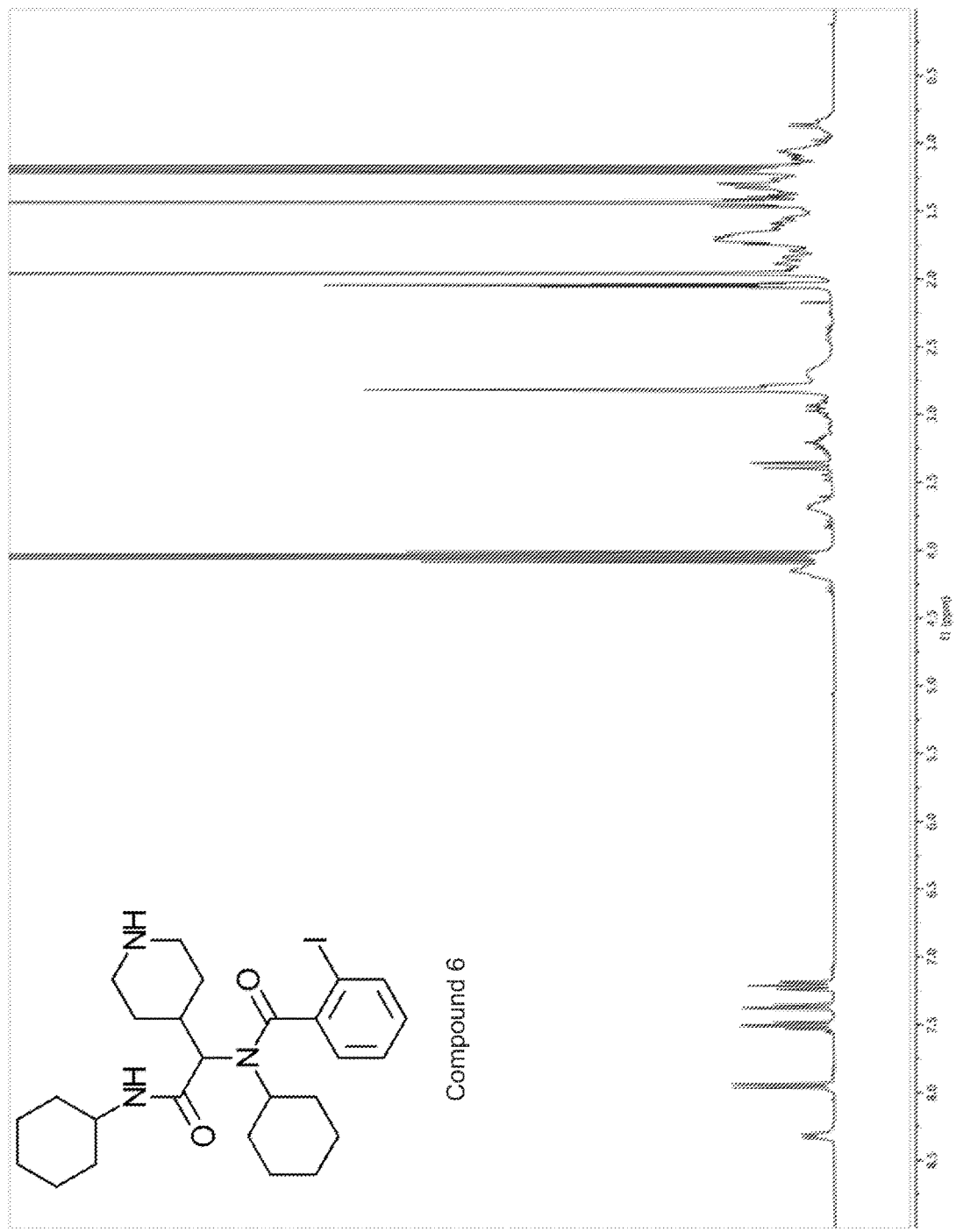
FIG. 3 represents the proton NMR of compound 6.
Figure 4:
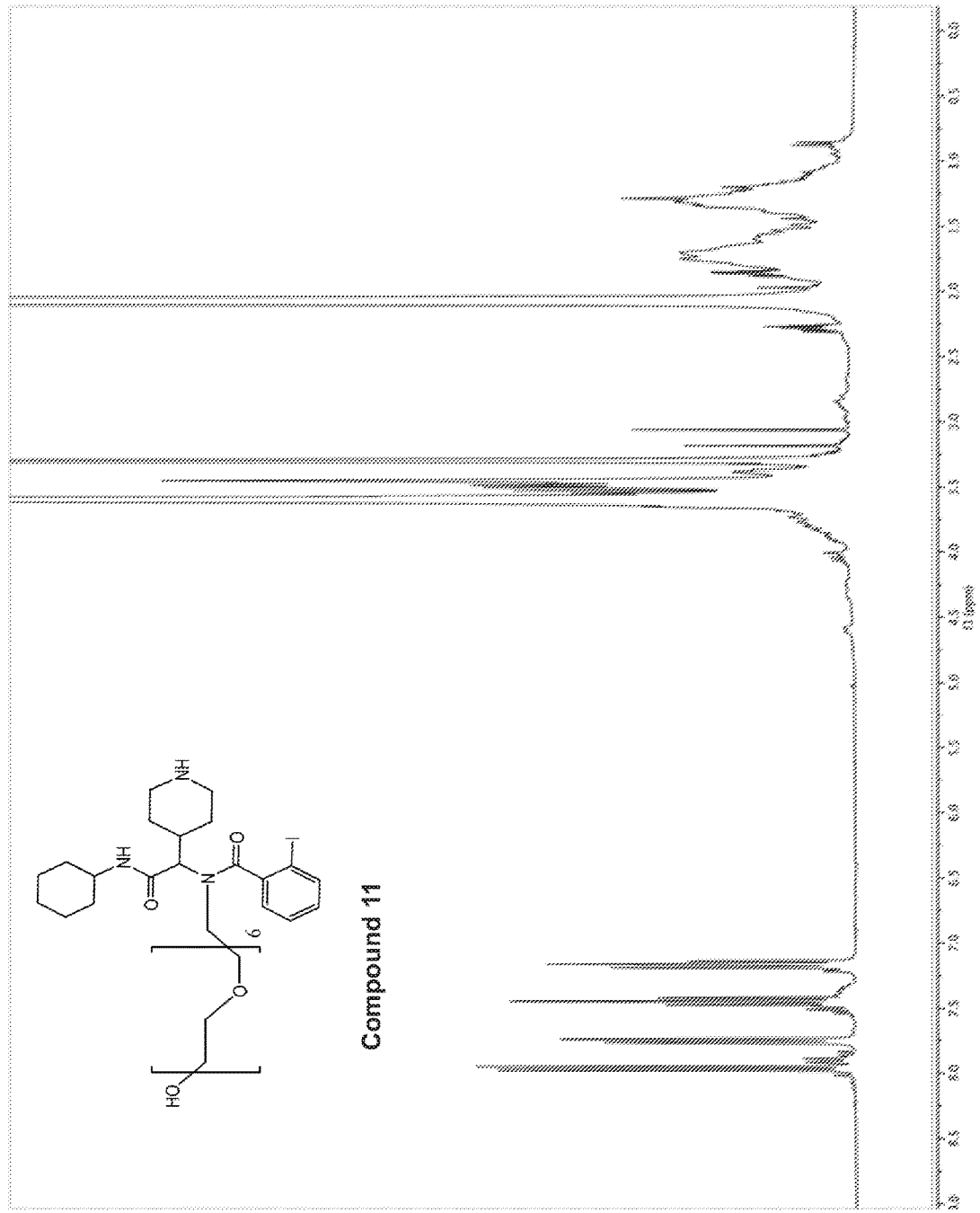
FIG. 4 represents the proton NMR of compound 11.

This invention is directed to compounds of Formula (I), to the pharmaceutically acceptable salts, esters, and prodrugs thereof, to their preparation, to pharmaceutical compositions comprising compounds of Formula I, and to their uses as antimicrobial agents. In one aspect, the instant invention is directed to a compound of Formula I:

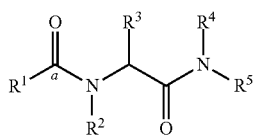

Formula I wherein:
$R^1$ represents a substituent selected from a group selected from polyethyleneglycol, hydrogen, $C_1$-$C_6$ alkyl, and aryl, wherein said $R^1$ substituents, except when $R^1$ represents hydrogen, are independently substituted with 1 to 3 substituents selected from a group consisting of H, X, S($C_{1-6}$ alkyl), O($C_{1-6}$ alkyl), and $CX_3$;

$R^2$ represents a substituent selected from a group consisting of $C_1$-$C_8$ alkyl, hydrogen, $C_3$-$C_8$ cycloalkyl, allyl, $C_3$-$C_8$ hetero cycloalkyl, polyethyleneglycol, propargyl, homopropargyl, aryl, heteroaryl, arylalkyl, and heteroarylalkyl, wherein each of said $R^2$ substituents, except when $R^2$ represents hydrogen, are independently substituted with 1-3 substituents selected from a group consisting of $C_1$-$C_6$ alkyl, H, $(CH_2$—O—$(CH_2)_{1-4})_6$—OH, $C_1$-$C_6$ alkenyl, $C_1$-$C_6$ alkynyl, OH, O($C_1$-$C_6$ alkyl), F, Cl, Br, I, $NO_2$, —C(=O)H, —C(=O)OH, —C(=O)O($C_1$-$C_6$ alkyl), —C(=O)$NH_2$, —C(=O)NH($C_1$-$C_6$ alkyl), and —C(=O)N($C_1$-$C_6$ alkyl)($C_1$-$C_6$ alkyl);

$R^3$ represents a substituent selected from a group consisting of $C_{1-6}$ alkyl-$NH_2$, hydrogen, $CH(CH_3)$—$NH_2$, $CH(CH_2CH_3)$—$NH_2$, $CH(CH_2CH_2CH_3)$—$NH_2$, $CH(CH_2CH_2CH_2CH_3)$—$NH_2$, $(CH_2)_{0-3}$— $C_3$-$C_8$ hetero cycloalkyl, $C_3$-$C_8$ cycloalkyl, propargyl, homopropargyl, polyethylene glycol, aryl, and heteroaryl, wherein each $R^3$ substituent, except when $R^3$ represents hydrogen, is independently substituted with 1-3 substituents independently selected from a group consisting of H, $C_1$-$C_6$ alkyl, OH, O($C_1$-$C_6$ alkyl), F, Cl, Br, I, $NO_2$, —C(=O)H, —C(=O)OH, —C(=O)O($C_1$-$C_6$ alkyl), —C(=O)$NH_2$, —C(=O)NH($C_1$-$C_6$ alkyl), and —C(=O)N($C_1$-$C_6$ alkyl)($C_1$-$C_6$ alkyl);

$R^4$ represents a substituent selected from the group consisting of $C_1$-$C_6$ alkyl, hydrogen, alkyl-aryl, $C_3$-$C_8$ cycloalkyl, arylalkyl, and heteroaryl-alkyl, wherein each of the $R^4$ substituents, except when $R^4$ represents hydrogen, is independently substituted with 1-3 substituents independently selected from the group consisting of $C_1$-$C_6$ alkyl, H, OH, O($C_1$-$C_6$ alkyl), F, Cl, Br, I, $NO_2$, —C(=O)H, —C(=O)OH, —C(=O)O($C_1$-$C_6$ alkyl), —C(=O)$NH_2$, —C(=O)NH($C_1$-$C_6$ alkyl), and —C(=O)N($C_1$-$C_6$ alkyl)($C_1$-$C_6$ alkyl);

$R^5$ is H or methyl; and
X is selected from Cl, I, Br, and F.

A preferred embodiment provides a compound of Formula I wherein, $R^1$ has at least one substituent ortho to the carbonyl group, wherein the at least one substituent is selected from the group consisting of X, S($C_1$-$C_6$ alkyl), O($C_{1-6}$ alkyl), and $CX_3$. Another preferred embodiment provides a compound of Formula I wherein the at least one substituent ortho to the carbonyl group is selected from the group consisting of X, O($C_{1-64}$ alkyl), and $CF_3$.

In yet another embodiment is provided a compound of Formula I wherein $R^2$ is selected from the group consisting of $C_1$-$C_6$ alkyl, $C_5$-$C_6$ cycloalkyl, polyethyleneglycol, propargyl, homopropargyl, phenyl, heteroaryl, aryl-$(CH_2)_{1-2}$—, and heteroaryl-$(CH_2)_{1-2}$—, wherein each of the said $R^2$ groups are independently substituted with 1-3 substituents independently selected from the group consisting of $(CH_2$—O—$(CH_2)_2)_6$—OH, $C_1$-$C_6$ alkyl, H, OH, O($C_1$-$C_6$ alkyl), F, Cl, Br, I, and $NO_2$, and a further preferred embodiment provides a compound of Formula I wherein $R^2$ is selected from the group consisting of $C_1$-$C_4$ alkyl, cyclo-hexyl, phenyl, o-iodophenyl, o-bromophenyl, o-chlorophenyl, o-fluorophenyl, o-methoxyphenyl, p-iodophenyl, p-bromophenyl, p-chlorophenyl, p-fluorophenyl, p-methoxyphenyl, benzyl, Ph$(CH_2)_2$—, Ph$_2$CHCH$_2$—, and —CH$(CH_3)$Ph.

Another preferred embodiment provides a compound of Formula I wherein $R^3$ is selected from the group consisting of $C_{1-4}$ alkyl-$NH_2$, $CH(CH_3)$—$NH_2$, $CH(CH_2CH_3)$—$NH_2$, $CH(CH_2CH_2CH_3)$—$NH_2$, $CH(CH_2CH_2CH_2CH_3)$—$NH_2$, $(CH_2)_{0-1}$—$C_4$-$C_6$-heterocycloalkyl, $C_4$-$C_6$ cycloalkyl, aryl, and heteroaryl, wherein each $R^3$ group is independently substituted with 1-2 substituents selected from the group consisting of $C_1$-$C_6$ alkyl, OH, O($C_1$-$C_6$ alkyl), F, Cl, Br, I, H, $NO_2$, —C(=O)H, —C(=O)OH, —C(=O)O($C_1$-$C_6$ alkyl), —C(=O)$NH_2$, —C(=O)NH($C_1$-$C_6$ alkyl), and —C(=O)N($C_1$-$C_6$ alkyl)($C_1$-$C_6$ alkyl).

Yet another preferred embodiment provides a compound of Formula I wherein $R^4$ is selected from the group consisting of $C_1$-$C_6$ alkyl, cyclo-hexyl, benzyl, wherein each of the alkyl, cyclo-hexyl, and benzyl group is substituted with 1-2 substituents independently selected from the group consisting of $C_1$-$C_3$ alkyl, H, OH, O($C_1$-$C_3$ alkyl), F, Cl, Br, and I.

A further preferred embodiment provides a compound of Formula I wherein, $R^1$ represents an aryl group, said aryl group substituted with X; $R^2$ is selected from $CH_2$—$(CH_2$—O—$(CH_2)_2)_6$—OH, $C_3$-$C_8$ cycloalkyl, and polyethyleneglycol; $R^3$ is selected from a group consisting of $C_{1-6}$ alkyl-$NH_2$, $CH(CH_3)—NH_2$, $CH(CH_2CH_3)—NH_2$, $CH(CH_2CH_2CH_3)—NH_2$, $CH(CH_2CH_2CH_2CH_3)—NH_2$, and $(CH_2)_{0-1}$-heterocyclyl; $R^4$ represents cyclo-hexyl; $R^5$ represents H; and X represents I, Cl, or Br.
Preferred compound of Formula I is selected from:
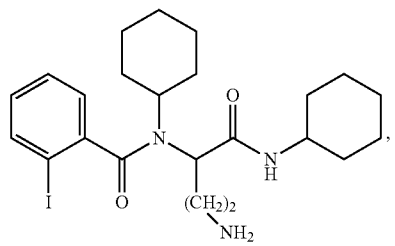
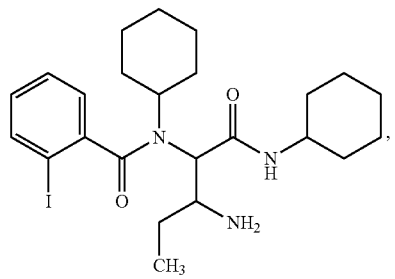
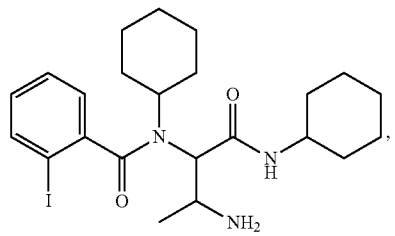
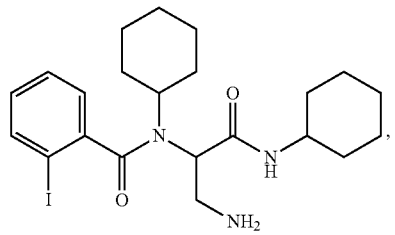
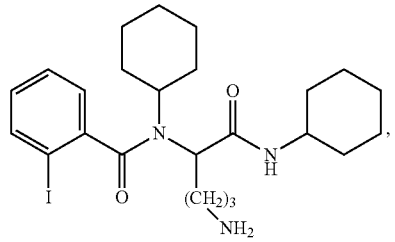
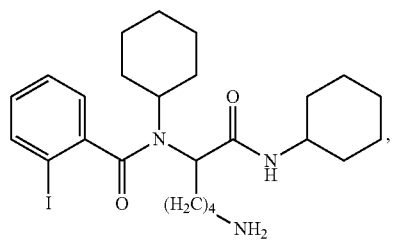
-continued
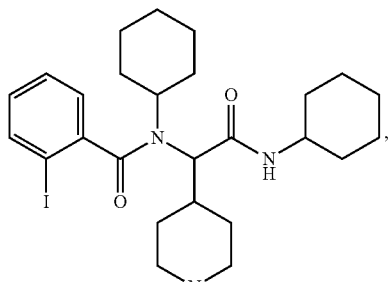
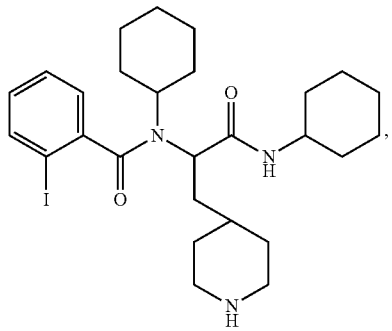
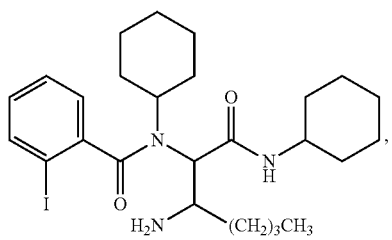
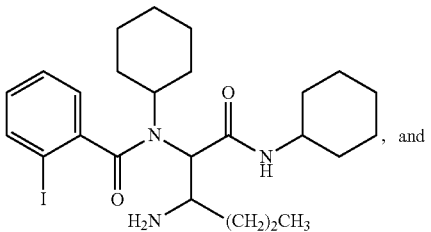, and
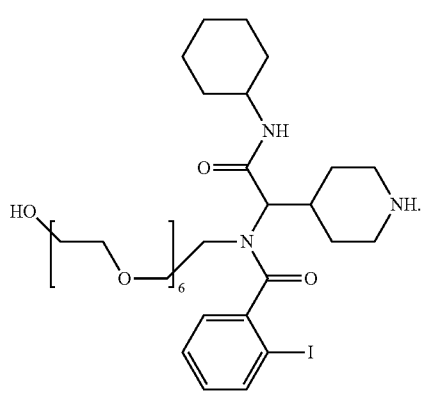.

Particularly preferred is a compound of Formula I selected from,

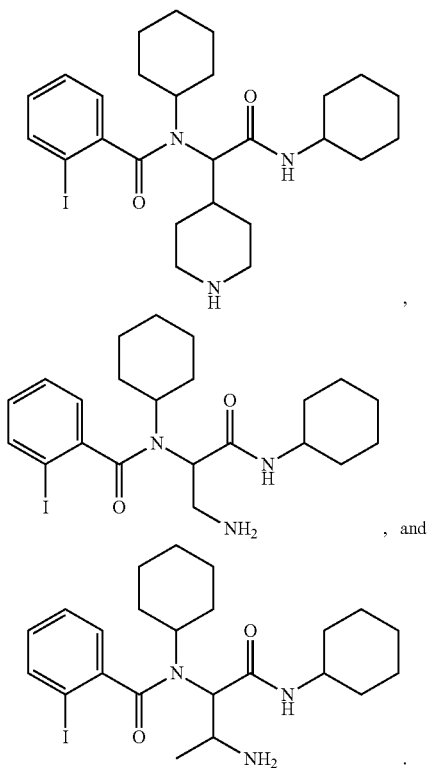

, and

Another aspect of the present invention provides a salt of a compound of Formula I, wherein the salt is an acid addition salt and is selected from the group consisting of sulfate, hydrogen sulfate, hydrochloric, hydrobromic, hydriodic, nitric, carbonic, sulfuric, phosphoric, formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid, and any combinations thereof.

Yet another aspect of the present invention provides a salt of a compound of Formula I wherein the salt is a base addition salt and is selected from the group consisting of calcium, magnesium, potassium, sodium, ammonium, zinc, a basic amine salt, and any combinations thereof, wherein the basic amine is selected from the group consisting of triethylamine, diisopropylethylamine, trimethylamine, N,N'-dibenzylethylene-diamine, chloroprocaine, choline, diethanolamine, ethylenediamine, meglumine, procaine and any combinations thereof.

Provides in yet another aspect of the present invention is a method of inhibiting N-acetylglucosaminidase in a cell, the method comprising contacting the cell with a compound of Formula I. Provided in a preferred aspect is a method of inhibiting a N-acetylglucosaminidase in the cytosol of a cell, the method comprising contacting the N-acetylglucosaminidase with any of the compounds of Formula I, wherein further preferred is a method wherein the N-acetylglucosaminidase is derived from a bacterium, or a fungus, and an even further preferred method is wherein the N-acetylglucosaminidase comprises an autolysin.

A further preferred aspect of the present invention provides a method of inhibiting N-acetylglucosaminidase wherein the bacterium is Gram-positive, and even further preferred dis a method wherein the Gram-positive bacterium is selected from the group consisting of *Streptococcus* sp., *Staphylococcus* sp., *Enterococcus* sp., *Corynebacterium* sp., *Listeria* sp., *Clostridium* sp., *Bacillus* sp, *Clostridium difficile*, *Streptococcus pneumoniae*, *Staphylococcus aureus*, vancomycin intermediate resistance *S. aureus* (VISA), *Enterococcus faecalis*, vancomycin resistant enterococci (VRE), *Streptococcus pyogenes*, *Bacillus anthracis*, *Corynebacterium diphtheria* and *Bacillus cereus*.

Another preferred embodiment provides a method of inhibiting N-acetylglucosaminidase wherein the bacterium is Gram-negative and is selected from a group consisting of *Salmonella* sp., *Escherichia* sp., *Klebsiella* sp., *Acinetobacter* sp., *Pseudomonas* sp., *Vibrio* sp. *Enterobacter* sp, *Salmonella enterica*, *Salmonella typhii*, *Escherichia coli*, *Klebsiella pneumoniae*, *Acinetobacter baumannii* and *Pseudomonas aerugenosa*.

Another aspect of the present invention provides a method of treating or preventing a bacterial infection in a subject comprising administering to a subject in need thereof a therapeutically effective amount of a compound of Formula I thereby treating or preventing a bacterial infection in a subject.

Another aspect of the present invention provides a method of treating or preventing a bacterial infection in a subject comprising administering to a subject in need thereof a therapeutically effective amount of a compound of Formula I along with at least one additional antibacterial agent.

Yet another aspect of the present invention provides a method of treating or preventing a bacterial infection in a subject comprising administering to a subject in need thereof a therapeutically effective amount of a compound of Formula I, wherein the subject is a mammal, and in particular wherein the mammal is a human.

Another aspect of the present invention provides a prepackaged pharmaceutical composition comprising a compound of Formula I, including a compound of Formula I in one of the preferred embodiments, a salt or solvate thereof and an instructional material for use thereof. A further preferred aspect provides a prepackaged pharmaceutical composition wherein the instructional material comprises instructions for preventing or treating a bacterial infection in a subject, and yet further preferred is a prepackaged pharmaceutical composition comprising an applicator.

In certain embodiments, the salt of any compound disclosed herein is an acid addition salt and is selected from the group consisting of sulfate, hydrogen sulfate, hydrochloric, hydrobromic, hydriodic, nitric, carbonic, sulfuric, phosphoric, formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, p-hydroxybutyric, salicylic, galactaric and galacturonic acid, and any combinations thereof.

The invention further provides a method of inhibiting a N-acetylglucosaminidase in a cell comprising contacting the cell with a compound of the invention. In certain embodiments, the cell is a bacterium, a fungus or a cancer cell. In yet other embodiments, the N-acetylglucosaminidase comprises an autolysin.

The invention also provides a method of inhibiting a N-acetylglucosaminidase in the cytosol of a cell. In certain embodiments, the method comprises contacting the N-acetylglucosaminidase with at least one compound of the invention. In other embodiments, the N-acetylglucosaminidase is derived from a bacterium, a fungus or a cancer cell. In yet other embodiments, the N-acetylglucosaminidase comprises an autolysin.

The invention further provides a method of treating or preventing a bacterial infection in a subject comprising administering to a subject in need thereof a therapeutically effective amount of at least one compound of the invention, thereby treating or preventing a bacterial infection in the subject.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the certain specific methods and materials are described.

As used herein, each of the following terms has the meaning associated with it in this section.

"About" as used herein when referring to a measurable value such as an amount, a temporal duration, and the like, is meant to encompass variations of ±20% or 10%, more advantageously ±5%, even more advantageously ±1%, and still more advantageously ±0.1% from the specified value, as such variations are appropriate to perform the disclosed methods.

A disease or disorder is "alleviated" if the severity of a symptom of the disease or disorder, the frequency with which such a symptom is experienced by a patient, or both, is reduced.

In one aspect, the terms "co-administered" and "co-administration" as relating to a subject refer to administering to the subject a compound of the invention or salt thereof along with a compound that may also treat the disorders or diseases contemplated within the invention. In one embodiment, the co-administered compounds are administered separately, or in any kind of combination as part of a single therapeutic approach. The co-administered compound may be formulated in any kind of combination, as mixtures of solids and liquids under a variety of solid, gel, and liquid formulations, and as a solution.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "disease" as used herein is a state of health of an animal wherein the animal cannot maintain homeostasis, and wherein if the disease is not ameliorated then the animal's health continues to deteriorate.

A "disorder" as used herein in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "DMSO" refers to dimethyl sulfoxide.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "GlcNAc" refers to N-acetylglucosamine.

As used herein, the term "GNT" refers to a GlcNAc triazole.

As used herein, the term "Gram-positive bacteria" are bacteria that give a positive result in the Gram stain test. Gram-positive bacteria take up the crystal violet stain used in the test, and then appear to be purple-colored when seen through a microscope. Gram-positive bacterial include *Streptococcus* sp., *Staphylococcus* sp., *Enterococcus* sp., *Corynebacterium* sp., *Listeria* sp., *Clostridium* sp. and *Bacillus* sp. Examples of Gram-positive bacteria include *Clostridium difficile* (also currently known as *Clostridioides difficile*), *Streptococcus pneumoniae*, *Staphylococcus aureus*, vancomycin intermediate resistance *S. aureus* (VISA), *Enterococcus faecalis*, vancomycin resistant enterococci (VRE), *Streptococcus pyogenes*, *Bacillus anthracis*, *Corynebacterium diphtheria* and *Bacillus cereus*.

As used herein, the term "Gram-negative bacteria" are a group of bacteria that do not retain the crystal violet stain used in the Gram staining method of bacterial differentiation. Gram-negative bacteria include *Salmonella* sp., *Escherichia* sp., *Klebsiella* sp., *Acinetobacter* sp., *Pseudomonas* sp., *Vibrio* sp. and *Enterobacter* sp. Examples of Gram-negative bacteria include *Salmonella enterica, Salmonella typhii, Escherichia coli, Klebsiella pneumoniae, Acinetobacter baumannii* and *Pseudomonas aerugenosa*.

The terms "patient," "subject" or "individual" are used interchangeably herein, and refer to any animal, or cells thereof whether in vitro or in situ, amenable to the methods described herein. In a non-limiting embodiment, the patient, subject or individual is a human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier is "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar, buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

The term "prevent," "preventing" or "prevention," as used herein, means avoiding or delaying the onset of symptoms associated with a disease or condition in a subject that has not developed such symptoms at the time the administering of an agent or compound commences. As used herein, the term "procure" or "procuring" as relating to a subject in need of being administered a therapeutically active compound refers to the act of synthesizing, packaging, prescribing, purchasing, providing or otherwise acquiring the compound so that the subject may be administered the compound.

By the term "specifically bind" or "specifically binds," as used herein, is meant that a first molecule preferentially binds to a second molecule (e.g., a particular receptor or enzyme), but does not necessarily bind only to that second molecule.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

As used herein, the term "alkyl," by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Certain specific examples include ($C_1$-$C_6$)alkyl, such as, but not limited to, ethyl, methyl, isopropyl, isobutyl, n-pentyl, n-hexyl and cyclopropylmethyl.

As used herein, the term "cycloalkyl," by itself or as part of another substituent means, unless otherwise stated, a cyclic chain hydrocarbon having the number of carbon atoms designated (i.e., $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Certain specific examples include ($C_3$-$C_6$)cycloalkyl, such as, but not limited to, cyclopropyl, cyclobutyl, cyclopentyl and cyclohexyl.

As used herein, the term "alkenyl," employed alone or in combination with other terms, means, unless otherwise stated, a stable mono-unsaturated or poly-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—$CH$=$CH_2$.

As used herein, the term "substituted alkyl," "substituted cycloalkyl," "substituted alkenyl" or "substituted alkynyl" means alkyl, cycloalkyl, alkenyl or alkynyl, as defined above, substituted by one or more substituents selected from the group consisting of halogen, —OH, alkoxy, tetrahydro-2-H-pyranyl, —$NH_2$, —$N(CH_3)_2$, (1-methyl-imidazol-2-yl), pyridin-2-yl, pyridin-3-yl, pyridin-4-yl, —C(=O)OH, trifluoromethyl, —C≡N, —C(=O)O($C_1$-$C_4$)alkyl, —C(=O)$NH_2$, —C(=O)NH($C_1$-$C_4$)alkyl, —C(=O)N(($C_1$-$C_4$)alkyl)$_2$, —$SO_2NH_2$, —C(=NH)$NH_2$, and —$NO_2$, advantageously containing one or two substituents selected from halogen, —OH, alkoxy, —$NH_2$, trifluoromethyl, —$N(CH_3)_2$, and —C(=O)OH, more advantageously selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. In certain embodiments, alkoxy includes ($C_1$-$C_3$)alkoxy, such as, but not limited to, ethoxy and methoxy.

As used herein, the term "halo" or "halogen" alone or as part of another substituent means, unless otherwise stated, a fluorine, chlorine, bromine, or iodine atom, advantageously, fluorine, chlorine, or bromine, more advantageously, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. In certain embodiments, aryl includes phenyl and naphthyl, in particular, phenyl.

As used herein, the terms "heterocycle", "heterocyclyl", "heterocyclic" or "hetero cycloalkyl", by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

The aforementioned listing of heterocyclyl, hetero cycloalkyl, and heteroaryl moieties is intended to be representative and not limiting.

As used herein, the term "substituted" means that an atom or group of atoms has replaced hydrogen as the substituent attached to another group.

In this disclosure, "comprises," "comprising," "containing" and "having" and the like can have the meaning ascribed to them in U.S. Patent law and can mean "includes," "including" and the liken "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.1, 5.3, 5.5, and 6. This applies regardless of the breadth of the range. The invention is based, at least in part, on the unexpected identification of novel small molecule inhibitors of N-acetylglucosaminidases. In certain embodiments, the compounds of the invention inhibit bacterial autolysins.

In one embodiment, the compounds of the invention are active against Gram-positive bacteria. In another embodiment, the Gram-positive bacterium is selected from the group consisting of *Streptococcus* sp., *Staphylococcus* sp., *Enterococcus* sp., *Corynebacterium* sp., *Listeria* sp., *Clostridium* sp. and *Bacillus* sp. In yet another embodiment, the Gram-positive bacterium is *Clostridium difficile* (now *Clostridiodes difficile, Streptococcus pneumoniae., Staphylococcus aureus*, vancomycin intermediate resistance *S. aureus* (VISA), *Enterococcus faecalis*, vancomycin resistant enterococci (VRE), *Streptococcus pyogenes, Bacillus anthracis, Corynebacterium diphtheria* or *Bacillus cereus*.

In another embodiment, the compounds of the invention are active against Gram-negative bacteria. In another embodiment, the Gram-negative bacterium is selected from the group consisting of *Salmonella* sp., *Escherichia* sp., *Klebsiella* sp., *Acinetobacter* sp., *Pseudomonas* sp., *Vibrio* sp. and *Enterobacter* sp. In yet another embodiment, the Gram-negative bacterium is *Salmonella enterica, Salmonella typhii, Escherichia coli, Klebsiella pneumoniae, Acinetobacter baumannii* or *Pseudomonas aerugenosa*.

As demonstrated herein, the compounds of the invention inhibit GlcNAcases, such as bacterial GlcNAcases.

In certain embodiments, the compounds of the invention exhibit whole-cell antibiotic activity. In other embodiments, the compounds modulate an extracellular enzyme, do not contain a reactive warhead susceptible to cleavage, and their target does not act on highly variable substrates. Without wishing to be limited by any theory, the molecular resistance mechanisms of efflux pumps, rapid chemical inactivation, and target substrate modification may be ineffective against the compounds of the invention.

Compounds and Compositions

The compounds herein disclosed have antibacterial activity against *S. pneumoniae, S. aureus* and/or *C. difficile*.

The invention further provides a pharmaceutical composition comprising at least one compound of the invention and a pharmaceutically acceptable carrier. In certain embodiments, the composition further comprises at least one additional antibacterial agent. In other embodiments, the at least one additional antibacterial agent comprises at least one agent selected from the group consisting of amoxicillin, azithromycin, biaxin, biocef, cefaclor, cinoxacin, ciprofloxacin, clindamycin, doryx, emgel, enoxacin, fortaz, gatifloxacin, levofloxacin, linezolid, maxaquin, moxifloxacin, neomycin, ofloxacin, penicillin, rifampin, sparfloxacin, streptomycin, sulfatrim, tetracycline, trovafloxacin, vancomycin and zotrim. In yet other embodiments, the compound and the agent are co-formulated in the composition.

The compounds of the invention may possess one or more stereocenters, and each stereocenter may exist independently in either the (R) or (S) configuration. In one embodiment, compounds described herein are present in optically active or racemic forms. The compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

In one embodiment, the compounds of the invention exist as tautomers. All tautomers are included within the scope of the compounds recited herein.

In one embodiment, the compounds of the invention exist as polymorphs. All polymorphs are included within the scope of the compounds recited herein.

In one embodiment, compounds described herein are prepared as prodrugs (see for example Hacker, et al., Pharmacology: Principles and Practice. Academic Press, Jun. 19, 2009. pp. 216-217). A "prodrug" is an agent converted into the parent drug in vivo. In one embodiment, upon in vivo administration, a prodrug is chemically converted to the biologically, pharmaceutically or therapeutically active form of the compound. In another embodiment, a prodrug is enzymatically metabolized by one or more steps or processes to the biologically, pharmaceutically or therapeutically active form of the compound.

In certain embodiments, sites on, for example, the aromatic ring portion of compounds of the invention are susceptible to various metabolic reactions. Incorporation of appropriate substituents on the aromatic ring structures may reduce, minimize or eliminate this metabolic pathway. Accordingly, in one embodiment, a prodrug is created by methods well known in the art, by which the appropriate substituent to decrease or eliminate the susceptibility of the aromatic ring to metabolic reactions is added, by way of example only, a deuterium, a halogen, or an alkyl group.

In one embodiment, the compounds described herein are labeled by other means, including, but not limited to, the use of chromophores or fluorescent moieties, bioluminescent labels, or chemiluminescent labels. Synthesis The compounds described herein, and other related compounds having different substituents, are synthesized using techniques and materials described herein and techniques known in the art such as those described, for example, in Fieser & Fieser's Reagents for Organic Synthesis, Volumes 1-17 (John Wiley and Sons, 1991); Rodd's Chemistry of Carbon Compounds, Volumes 1-5 and Supplements (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4* Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compounds as described herein are modified by the use of appropriate reagents and conditions, for the introduction of the various moieties found in the formula as provided herein. Compounds described herein are synthesized using any suitable procedures starting from compounds that are available from commercial sources, or are prepared using procedures described herein or known in the art.

In one embodiment, reactive functional groups, such as hydroxyl, amino, imino, thio or carboxy groups, are protected in order to avoid their unwanted participation in reactions.

Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In one embodiment, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxy benzyl, while coexisting amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

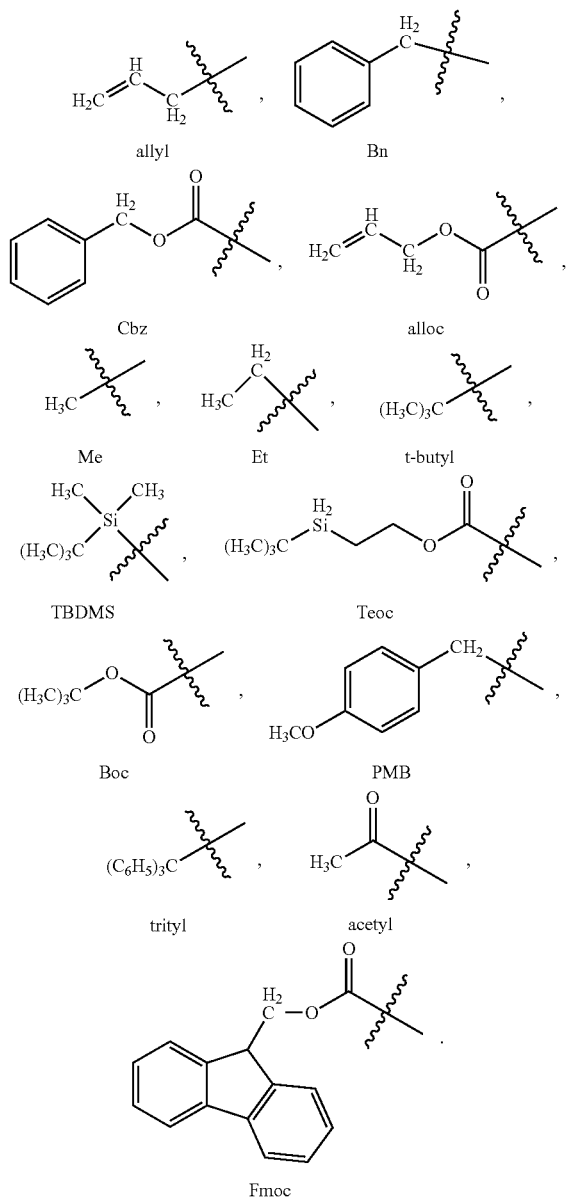

Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

The compounds of the invention may be prepared according to the general methodology illustrated in the synthetic schemes described below. The reagents and conditions described herein may be modified to allow the preparation of the compounds of the invention, and such modifications are known to those skilled in the art. The scheme included herein are intended to illustrate but not limit the chemistry and methodologies that one skilled in the art may use to make compounds of the invention. Salts The compounds described herein may form salts with acids, and such salts are included in the present invention. In one embodiment, the salts are pharmaceutically acceptable salts. The term "salts" embraces addition salts of free acids that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, p-hydroxybutyric, salicylic, galactaric and galacturonic acid.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts.

Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

Methods

The invention provides a method of inhibiting a N-acetylglucosaminidase in a cell. In certain embodiments, the method comprises contacting the cell with at least one compound of the invention. In other embodiments, the cell is a bacterium, a fungus or a cancer cell. In yet other embodiments, the N-acetylglucosaminidase comprises an autolysin.

The invention also provides a method of inhibiting a N-acetylglucosaminidase in the cytosol of a cell. In certain embodiments, the method comprises contacting the N-acetylglucosaminidase with at least one compound of the invention. In other embodiments, the N-acetylglucosaminidase is derived from a bacterium, a fungus or a cancer cell.

The invention further provides a method of treating or preventing a bacterial infection in a subject in need thereof. In certain embodiments, the method comprises administering a therapeutically effective amount of at least one compound of the invention to the subject.

In yet other embodiments, the subject is further administered at least one additional antibacterial agent. In yet other embodiments, the at least one additional antibacterial agent comprises at least one agent selected from the group consisting of amoxicillin, azithromycin, biaxin, biocef, cefaclor, cinoxacin, ciprofloxacin, clindamycin, doryx, emgel, enoxacin, fortaz, gatifloxacin, levofloxacin, linezolid, maxaquin, moxifloxacin, neomycin, ofloxacin, penicillin, rifampin, sparfloxacin, streptomycin, sulfatrim, tetracycline, trovafloxacin, vancomycin and zotrim.

In certain embodiments, the compound of the invention and the additional agent are separately administered to the subject. In other embodiments, the compound and the agent are co-administered to the subject. In yet other embodiments, the compound and the agent are co-formulated. In yet other embodiments, the compound is administered to the subject by at least one route selected from the group consisting of intravenous, oral, inhalational, rectal, vaginal, transdermal, intranasal, buccal, sublingual, parenteral, intrathecal, intragastrical, ophthalmic, pulmonary and topical routes. In yet other embodiments, the subject is a mammal. In yet other embodiments, the mammal is a human. In yet other embodiments, the method further comprises procuring the at least one compound of the invention for the subject. Kits The invention includes a kit comprising a compound of the invention, an applicator, and an instructional material for use thereof. The instructional material included in the kit comprises instructions for preventing or treating a disorder or disease contemplated within the invention in a subject. The instructional material recites the amount of, and frequency with which, the compound of the invention should be administered to the subject. In certain embodiments, the kit further comprises at least one additional antibacterial agent. Combination Therapies In certain embodiments, the compounds of the invention are useful in the methods of the invention in combination with at least one additional agent useful for treating or preventing bacterial infection. This additional agent may comprise compounds identified herein or compounds, e.g., commercially available compounds, known to treat, prevent or reduce the symptoms of bacterial infection.

Non-limiting examples of additional agents contemplated within the invention include amoxicillin, azithromycin, biaxin, biocef, cefaclor, cinoxacin, ciprofloxacin, clindamycin, doryx, emgel, enoxacin, fortaz, gatifloxacin, levofloxacin, linezolid, maxaquin, moxifloxacin, neomycin, ofloxacin, penicillin, rifampin, sparfloxacin, streptomycin, sulfatrim, tetracycline, trovafloxacin, vancomycin and zotrim.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, in particular a mammal, more particularly a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder contemplated in the invention.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is advantageous to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In one embodiment, the compounds/compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 μg to about 10,000 mg, about 20 μg to about 9,500 mg, about 40 μg to about 9,000 mg, about 75 μg to about 8,500 mg, about 150 μg to about 7,500 mg, about 200 μg to about 7,000 mg, about 3050 μg to about 6,000 mg, about 500 μg to about 5,000 mg, about 750 μg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent may then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of a disease or disorder contemplated in the invention. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition. The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin.

Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see Constanza, U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum.

Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. In particular, it is advantageously present in an amount from about 0.0005% to about 5% of the composition; more particularly, it is advantageously present in an amount of from about 0.001% to about 1% of the composition. Such compounds may be synthetically- or naturally derived.

Buccal Administration

A pharmaceutical composition of the invention may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers and may further comprise one or more of the additional ingredients described herein. The examples of formulations described herein are not exhaustive and it is understood that the invention includes additional modifications of these, and other formulations not described herein, but which are known to those of skill in the art.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20 ˚C) and which is liquid at the rectal temperature of the subject (i.e., about 37 ˚C in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In one embodiment, the formulations of the present invention may be, but are not limited to, short-term, rapid-offset, as well as controlled, for example, sustained release, delayed release and pulsatile release formulations. The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of a disease or disorder contemplated in the invention. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies advantageously within a range of circulating concentrations that include the $ED_{50}$ with minimal toxicity. The dosage optionally varies within this range depending upon the dosage form employed and the route of administration utilized.

Those skilled in the art will recognize or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein. Materials and Methods Thin layer chromatography was performed on Merck silica gel 60 F254 precoated glass plates and spots were visualized by UV light. Column chromatography was performed with DAVISIL Chromatographic Silica Media LC60A 35-70 micron, Silicycle media, or on a Teledyne ISCO CombiFlash Rf purification system. Solvents were evaporated under reduced pressure at 30-40° C. Electrospray ionization high-resolution mass spectra (ESI-HRMS) were obtained using a Jeol JMS-600H spectrometer in positive ion mode. 1H, 13C, COSY, and HSQC spectra were recorded on a Bruker Avance III HD Ascend 600 MHz or Advance 400 MHz spectrometer. Chemical shifts are reported on a δ scale relative to residual solvent peaks in either (CD3)2CO (1H=δ 2.05 ppm, 13C=δ 29.84 ppm) or (CD3)2SO (1H=δ 2.50 ppm, 13C=δ 39.52 ppm) 0.19F NMR chemicals shifts were externally referenced to C6H5CF3 (−63.72 ppm). All NMR data are reported in the form: chemical shift (S ppm), (multiplicity (s=singlet, d=doublet, dd=doublet of doublets, t=triplet, tt=triplet of triplets, q=quartet, qt=quartet of triplets, m=multiplet, br=broad), coupling constant (Hz), integration, and assignment). The diamide products from the Ugi reaction can exist as mixtures of the amide bond rotamers, as well as atropisomers about the acid-derived phenyl ring. Partial assignments are provided. Representative Ugi Procedure Terminal alkynes were prepared using the Ugi four-component condensation reaction. The Ugi condensation is a one-pot reaction that combines an acid, an amine, an aldehyde, and an isocyanide to form a dipeptide. The general Ugi reaction utilized is shown in Scheme 2. In certain non-limiting embodiments, propargylamine and n-butyl isocyanide were held constant for all Ugi-derived compounds. The first four Ugi compounds synthesized held all aspects of the fgba structure (Scheme 3) constant while varying the substituent on the benzyl ring of the acid. The last two Ugi compounds instead varied only the aldehyde substituent while retaining the iodobenzoic acid. The synthetic schemes and final structures of non-limiting Ugi compounds are illustrated in the Scheme below:

Scheme 1: Synthesis of N-Boc protected Di-amide (5)

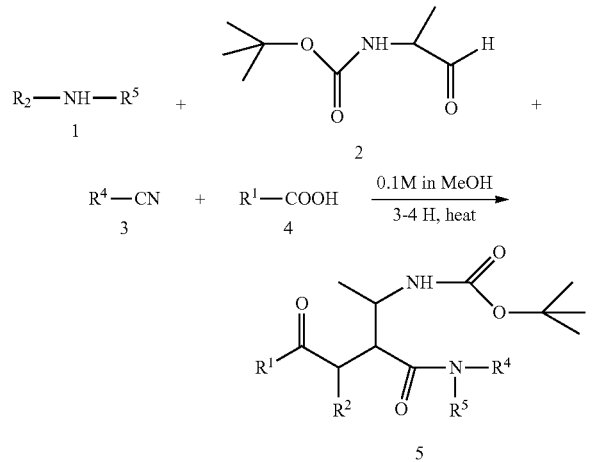

A 0.1 M solution of each reactant—amine (1), aldehyde (2), isocyanide (3) and acid (4)—in MeOH was prepared. Amine (5.0 mL of 0.1 M) and aldehyde (5.0 mL of 0.1 M) were stirred in a capped scintillation vial for 30 min. at 40° C. Next, the isocyanide (5.0 mL of 0.1 M) was added to this solution and the reaction mixture was stirred for additional 20 minutes at 50° C. Lastly the acid (5.0 mL of 0.1M) was added and the reaction mixture was continuously stirred at 55° C. for 3-5 hours. The progress of the reaction was monitored by TLC plate using UV-light, p-anisaldehyde and/or potassium permanganate staining for visualization. When the reaction was complete the solvent was removed in a Centrifan™ evaporator and the crude product was dried under high vacuum until all methanol had evaporated. The dried crude product was dissolved in 30 mL of ethyl acetate. The organic layer was then extracted with 1 M HCl (2×), H$_2$O, saturated NaHCO$_3$ (2×), H$_2$O and brine (2×). The organic layer was then dried with Na$_2$SO$_4$ and the solvent was evaporated on a rotary evaporator. The final product (5) was dried under high vacuum. Individual yields and physical descriptions are provided below. All reactions were carried out at a scale of 0.5 mmol.

Scheme II: Deprotection of N-Boc protected Di-amide

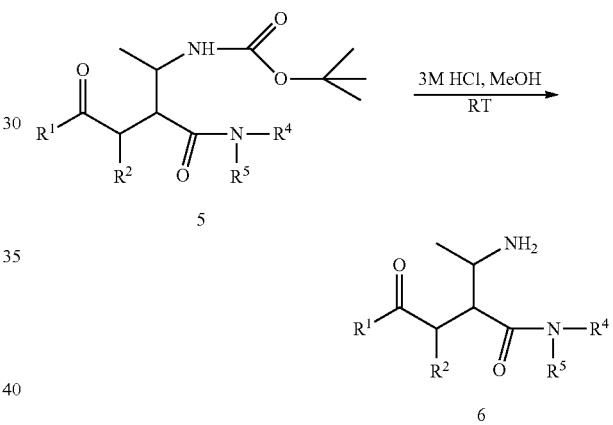

N-Boc-diamide (5) (0.3 mmol) was suspended in 20 mL of MeOH. To the suspension 20 mL of 3 M HCl in MeOH was added and stirred for 15-60 min at room temperature. The progress of the reaction was monitored by TLC plate using UV-light or ninhydrin staining for visualization. When the reaction was complete, solvent was evaporated to dryness under vacuum and the resulting residue dissolved in ether. The precipitated diamide compound of Formula I (6) was collected by filtration and dried in vacuo.

Compounds in Table I were synthesized using the procedure(s) discussed above:

TABLE I

| Ex | Compound | Name |
|---|---|---|
| 1 | (structure) | N-(4-amino-1-(cyclohexylamino)-1-oxobutan-cyclohexyl-2-iodobenzamide |

TABLE I-continued

| Ex | Compound | Name |
|---|---|---|
| 2 | 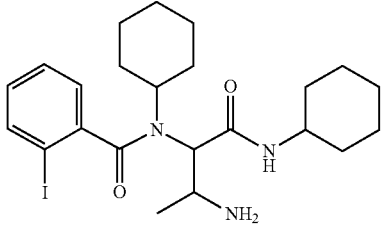 [SMILES: CC(N)C(C(=O)NC1CCCCC1)N(C(=O)c1ccccc1I)C1CCCCC1] | N-(4-amino-1-(cyclohexylamino)-1-oxobutan-cyclohexyl-2-iodobenzamide |
| 3 | 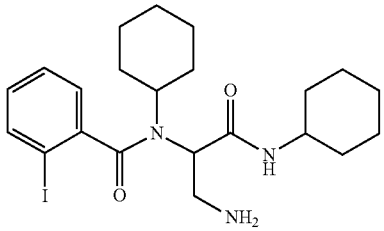 [SMILES: NCC(C(=O)NC1CCCCC1)N(C(=O)c1ccccc1I)C1CCCCC1] | N-(3-amino-1-(cyclohexylamino)-1-oxopropan-2-yl)-N-cyclohexyl-2-iodobenzamide |
| 4 | 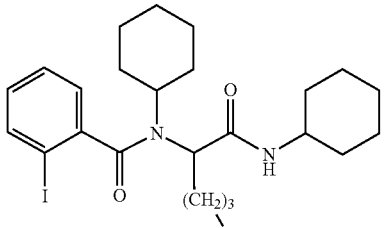 | N-(5-amino-1-(cyclohexylamino)-1-oxopentan-2-yl)-N-cyclohexyl-2-iodobenzamide |
| 5 | 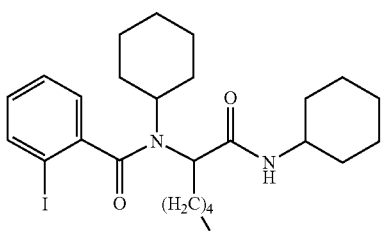 | N-(6-amino-1-(cyclohexylamino)-1-oxohexan-2-yl)-N-cyclohexyl-2-iodobenzamide |
| 6 | 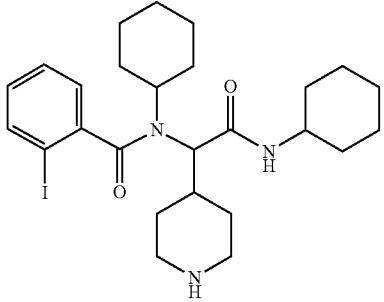 [SMILES: O=C(NC1CCCCC1)C(C1CCNCC1)N(C(=O)c1ccccc1I)C1CCCCC1] | N-cyclohexyl-N-(2-(cyclohexylamino)-2-oxo-1-(piperidin-4-yl)ethyl)-2-iodobenzamide |

TABLE I-continued

| Ex | Compound | Name |
|---|---|---|
| 7 | | N-cyclohexyl-N-(1-(cyclohexylamino)-1-oxo-3-(piperidin-4-yl)propan-2-yl)-2-iodobenzamide |
| 8 | | N-(3-amino-1-(cyclohexylamino)-1-oxopentan-2-yl)-N-cyclohexyl-2-iodobenzamide |
| 9 | | N-(3-amino-1-(cyclohexylamino)-1-oxoheptan-2-yl)-N-cyclohexyl-2-iodobenzamide |
| 10 | | N-(3-amino-1-(cyclohexylamino)-1-oxohexan-2-yl)-N-cyclohexyl-2-iodobenzamide |
| 11 | | |

Antimicrobial Testing

1. Bacterial Strains and Growth Conditions

*Bacillus subtilis* ATCC 11775 was plated on agar from a 20% glycerol stock solution stored at −80'° C. Inoculated plates were then incubated at 37° C. under aerobic conditions for 16 hours. Single cultures were transferred to Nutrient Broth (NB) and cultured for 16 hours under the same conditions. Samples of first passage cultures that exhibited growth were transferred again to fresh NB media and cultured for 6 hours under identical conditions. Second passage cells were standardized to O.D. 600 nm=1

2. Antimicrobial Screening Assay

Antimicrobial Screening Assays were conducted using one of the following two procedures:

Procedure I:

The resazurin microtiter assay procedure described by Palomino and coworkers is used for assessing antimicrobial activity (Palomino, et al., 2002, Antimicrob Agents Chemother. 46:2720-2722). The assay is performed in LB broth. Resazurin sodium salt powder is prepared in distilled water and filter sterilized at 0.001% (w/v) for MIC assays and at 0.01% (w/v) for single concentration assays. Compounds are first screened in MIC assays to assess whether growth inhibition is dependent on inhibitor concentration. The plates are incubated for 30 min under aerobic conditions. Growth controls containing no inhibitory compound, sterility controls without inoculation, and controls containing a known antibiotic, chloramphenicol, are also included. The innoculum was prepared from second passage cultures in Nutrient Broth (NB) and standardized to $O.D._{600nm}=1.0$ and the wells inoculated with a 1:20 dilution. Serial two-fold dilutions of each compound in 100 μL of medium are prepared directly in 96 well plates at concentrations ranging from 250 μM to 7 μM. After incubation 30 μL of resazurin solution is added to each well and incubated for 30 min. A change in color from blue to pink indicates reduction of resazurin, and therefore bacterial growth. Minimum inhibitory concentration (MIC) was determined as the lowest drug concentration that prevented the color change from blue to pink. Inhibition was quantified by observation of color change. Further studies were carried out at a single inhibitor concentration of 250 μM. The plates were incubated for 4 h under aerobic conditions with the same controls. After incubation 30 μL of resazurin solution was added to each well and incubated for 60 min. Inhibition was quantified by fluorescence readings from plate reader SAFIRE, Firmware: V 2.2008/02 Safire. Excitation wavelength set to 560 nm, emission wavelength set to 590 nm. Well containing dye and non-inoculated cells was used as gain set. Plates are held at 37° C. and fluorescence measurements are taken at 0, 5, 10, 20, 30, and 60 min after addition of dye. Lower fluorescence values correlate to greater degrees of inhibition.

Procedure II:

Antimicrobial Assay (MIC) values were determined using the rezasurin method.

Briefly, second passage cells of B. subtilis 11774 were grown in LB media and standardized to an $OD_{600\ nm}=1.0$. Diamides were analyzed via serial dilution into LB media in microtitre plates. Microtitre plates were innoculated with a 1/20 dilution of the $OD_{600\ nm}=1.0$ cell culture. Cultures were grown statically for 4 h at 37° C., followed by addition of 30 μL of a 0.01% (m/v) solution of resazurin. The plates were allowed to incubate for 15 min to allow stabilization of color production. MICs were read directly off the plate or via fluorescence ($\lambda_{ex}$ 560 nm, $\lambda_{em}$ 590 nm). MICs were recorded as the lowest concentration that inhibited growth.

Resazurin In Vivo Assay

Selected compounds of the invention are assayed for antibiotic activity. The initial screens are performed against whole cells, and not purified enzymes, in order to eliminate those compounds that did not reduce bacterial growth Compounds are tested in vivo for their capacity to inhibit B. subtilis growth. In order to determine growth inhibition, a resazurin whole-cell assay was used (Kuhn, et al., 2014, Medchemcomm 5:1213-1217). Briefly, second-passage bacteria are incubated with inhibitor in a 96-well plate for four hours, then resazurin dye is added and color/fluorescence change is observed. The resazurin is naturally a blue color, but with reductive species produced during bacterial growth, it is reduced to resorufin, which appears pink. Resorufin is also fluorescent and can be measured by a plate-reader. The disclosures of each and every patent, patent application, and publication cited herein are hereby incorporated herein by reference in their entirety.

Although the invention has been disclosed and described with reference to specific embodiments, it is apparent that other embodiments and variations of this invention may be devised by others skilled in the art without departing from the true spirit and scope of the invention. The appended claims are intended to be construed to include all such embodiments and equivalent variations.

MIC Assay Results for compounds of Formula I are provided in Table II below:

TABLE II

| Compound/Example # | Apparent MIC Value |
|---|---|
| 2 | 5 μM (B. subtilis) |
| 3 | 5 μM (B. subtilis) |
| 6 | 5 μM (E. Coli) |

The invention claimed is:
1. A compound of Formula I

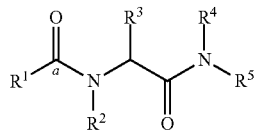

Formula I wherein:
$R^1$ represents aryl, wherein aryl is substituted with 1 to 3 substituents selected from a group consisting of H, —X, S($C_{1-6}$ alkyl), O($C_{1-6}$ alkyl), and $CX_3$;
$R^2$ is selected from the group consisting of $C_1$-$C_8$ alkyl, $C_3$-$C_8$ cycloalkyl, $C_3$-$C_8$ hetero cycloalkyl, and polyethyleneglycol, wherein each of said $R^2$ groups are independently substituted with 1-3 substituents selected from a group consisting of $C_1$-$C_6$ alkyl, H, $C_1$-$C_6$ alkenyl, $(CH_2$—O—$(CH_2)_{1-4})_6$—OH, $C_1$-$C_6$ alkynyl, OH, O($C_1$-$C_6$ alkyl), F, Cl, Br, I, $NO_2$, —C(=O)H, —C(=O)OH, —C(=O)O($C_1$-$C_6$ alkyl), —C(=O)$NH_2$, —C(=O)NH($C_1$-$C_6$ alkyl), and —C(=O)N($C_1$-$C_6$ alkyl)($C_1$-$C_6$ alkyl);
$R^3$ is selected from a group consisting of $C_{1-6}$ alkyl-$NH_2$, CH($CH_3$)—$NH_2$, CH($CH_2CH_2CH_3$)—$NH_2$, CH($CH_2CH_2CH_2CH_3$)—$NH_2$, $(CH_2)_{0-3}$— $C_3$-$C_8$ hetero cycloalkyl wherein each $R^3$ group is independently substituted with 1-3 substituents independently selected from a group consisting of H, $C_1$-$C_6$ alkyl, OH, O($C_1$-$C_6$ alkyl), F, Cl, Br, I, $NO_2$, —C(=O)H, —C(=O)OH, —C(=O)O($C_1$-$C_6$ alkyl), —C(=O)$NH_2$, —C(=O)NH($C_1$-$C_6$ alkyl), and —C(=O)N($C_1$-$C_6$ alkyl)($C_1$-$C_6$ alkyl);
$R^4$ is selected from the group consisting of $C_1$-$C_6$ alkyl, $C_3$-$C_8$ cycloalkyl, arylalkyl, and heteroaryl-alkyl, wherein each of the $R^4$ groups is independently substituted with 1-3 substituents independently selected from the group consisting of $C_1$-$C_6$ alkyl, H, OH, O(C$_1$-C$_6$ alkyl), F, Cl, Br, I, NO$_2$, —C(=O)H, —C(=O)OH, —C(=O)O(C$_1$-C$_6$ alkyl), —C(=O)NH$_2$, —C(=O)NH(C$_1$-C$_6$ alkyl), and —C(=O)N(C$_1$-C$_6$ alkyl)(C$_1$-C$_6$ alkyl);

R$^5$ is H or methyl; and

X is selected from Cl, I, Br, and F.

2. The compound of claim 1, wherein in R$^1$ has at least one substituent ortho to the carbonyl group, wherein the at least one substituent is selected from the group consisting of X, O(C$_{1-6}$ alkyl), and CX$_3$; and X is selected from I and Br.

3. The compound of claim 1, wherein R$^2$ is represents C$_1$-C$_6$ alkyl, substituted with 1-3 substituents independently selected from the group consisting of (CH$_2$—O—(CH$_2$)$_2$)$_6$—OH, C$_1$-C$_6$ alkyl, H, OH, and O(C$_1$-C$_6$ alkyl).

4. The compound of claim 1, wherein R$^3$ is selected from the group consisting of C$_1$-C$_4$ alkyl-NH$_2$, CH(CH$_3$)—NH$_2$, CH(CH$_2$CH$_3$)—NH$_2$, CH(CH$_2$CH$_2$CH$_3$)—NH$_2$, CH(CH$_2$CH$_2$CH$_2$CH$_3$)—NH$_2$, (CH$_2$)$_{0-1}$—C$_4$-C$_6$-heterocycloalkyl, wherein each R$^3$ group is independently substituted with 1-2 substituents selected from the group consisting of C$_1$-C$_6$ alkyl, OH, O(C$_1$-C$_6$ alkyl), F, Cl, Br, I, H, NO$_2$, —C(=O)H, —C(=O)OH, —C(=O)O(C$_1$-C$_6$ alkyl), —C(=O)NH$_2$, —C(=O)NH(C$_1$-C$_6$ alkyl), and —C(=O)N(C$_1$-C$_6$ alkyl)(C$_1$-C$_6$ alkyl).

5. The compound of claim 1, wherein R$^4$ is selected from the group consisting of C$_1$-C$_6$ alkyl, cyclo-hexyl, benzyl, wherein each of the alkyl, cyclo-hexyl, and benzyl group is substituted with 1-2 substituents independently selected from the group consisting of C$_1$-C$_3$ alkyl, H, OH, O(C$_1$-C$_3$ alkyl), F, Cl, Br, and I.

6. The compound of claim 1, wherein

R$^1$ represents an aryl group, said aryl group substituted with X;

R$^2$ represents C$_4$-C$_8$ cycloalkyl;

R$^3$ is selected from a group consisting of C$_{1-6}$ alkyl-NH$_2$, CH(CH$_3$)—NH$_2$, CH(CH$_2$CH$_3$)—NH$_2$, CH(CH$_2$CH$_2$CH$_3$)—NH$_2$, CH(CH$_2$CH$_2$CH$_2$CH$_3$)—NH$_2$, and (CH$_2$)$_{0-1}$-heterocyclyl;

R$^4$ represents cyclo-hexyl;

R$^5$ represents H; and

X represents I, Cl, or Br.

7. A compound of Formula I of claim 1 selected from:

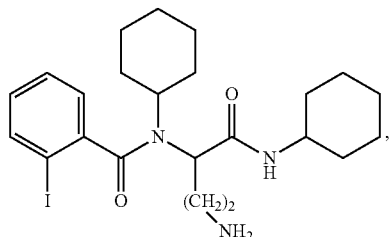

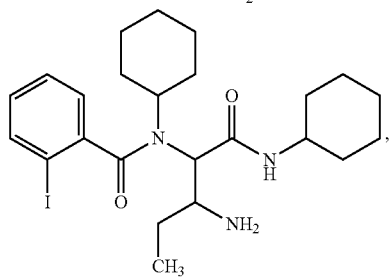

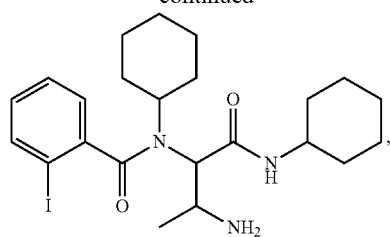

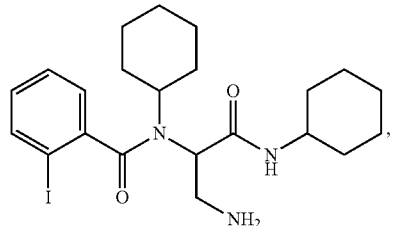

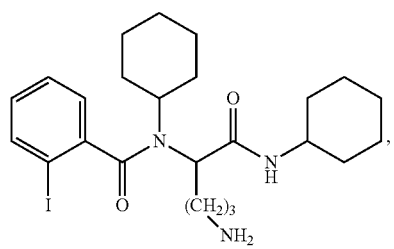

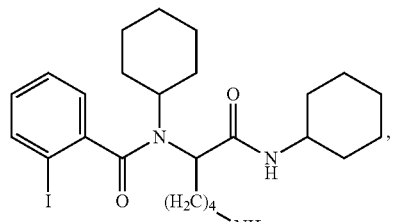

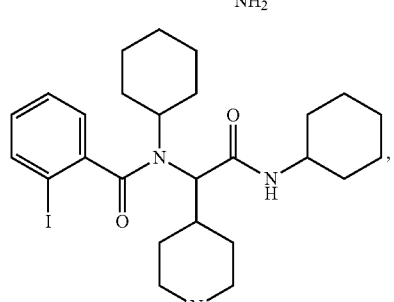

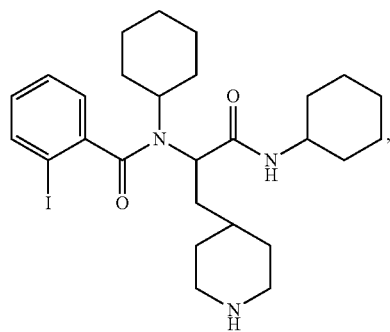

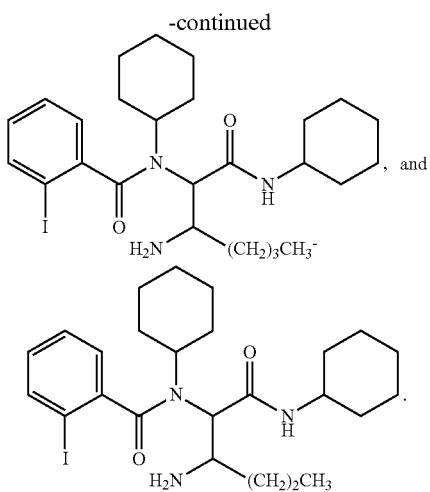

8. The compound of claim 1, wherein the salt of compound I is an acid addition salt and is selected from the group consisting of sulfate, hydrogen sulfate, hydrochloric, hydrobromic, hydriodic, nitric, carbonic, sulfuric, phosphoric, formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid, and any combinations thereof.

9. The compound of claim 1, wherein the salt is a base addition salt and is selected from the group consisting of calcium, magnesium, potassium, sodium, ammonium, zinc, a basic amine salt, and any combinations thereof, wherein the basic amine is selected from the group consisting of triethylamine, diisopropylethylamine, trimethylamine, N,N'-dibenzylethylene-diamine, chloroprocaine, choline, diethanolamine, ethylenediamine, meglumine, procaine and any combinations thereof.

10. A method of inhibiting a N-acetylglucosaminidase in a cell, the method comprising contacting the cell with a compound of claim 1.

11. The method of claim 10, comprising inhibiting a N-acetylglucosaminidase in the cytosol of a cell.

12. The method of claim 11, wherein the N-acetylglucosaminidase comprises an autolysin.

13. A method of treating a bacterial infection in a subject comprising administering to a subject in need thereof a therapeutically effective amount of a compound of claim 1, thereby treating or preventing a bacterial infection in a subject.

14. The method of claim 13, wherein the bacterium is Gram-positive.

15. The method of claim 14, wherein the Gram-positive bacterium is selected from the group consisting of *Streptococcus* sp., *Staphylococcus* sp., *Enterococcus* sp., *Corynebacterium* sp., *Listeria* sp., *Clostridium* sp. and *Bacillus* sp.

16. The method of claim 13, wherein the bacterium is Gram-negative.

17. The method of claim 16, wherein the Gram-negative bacterium is selected from the group consisting of *Salmonella* sp., *Escherichia* sp., *Klebsiella* sp., *Acinetobacter* sp., *Pseudomonas* sp., *Vibrio* sp. and *Enterobacter* sp.

18. The method of claim 13, wherein the subject is further administered at least one additional antibacterial agent.

19. The method of claim 13, wherein the subject is a mammal.

* * * * *